(12) United States Patent
Noyes

(10) Patent No.: US 11,156,618 B1
(45) Date of Patent: *Oct. 26, 2021

(54) RAPID MEASUREMENT OF TOTAL VITAMIN D IN BLOOD

(71) Applicant: Labrador Diagnostics LLC, Newark, CA (US)

(72) Inventor: Tina Noyes, East Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,955

(22) Filed: Jun. 4, 2018

Related U.S. Application Data

(63) Continuation of application No. 15/658,920, filed on Jul. 25, 2017, now Pat. No. 10,073,103, which is a continuation of application No. 14/819,259, filed on Aug. 5, 2015, now abandoned, which is a continuation of application No. 14/203,239, filed on Mar. 10, 2014, now abandoned.

(60) Provisional application No. 61/776,641, filed on Mar. 11, 2013.

(51) Int. Cl.
  *G01N 31/00* (2006.01)
  *G01N 33/53* (2006.01)
  *G01N 33/82* (2006.01)

(52) U.S. Cl.
  CPC ......... *G01N 33/82* (2013.01); *G01N 2333/95* (2013.01)

(58) Field of Classification Search
  None
  See application file for complete search history.

(56) References Cited

U.S. PATENT DOCUMENTS

| | | | |
|---|---|---|---|
| 3,962,039 A | 6/1976 | Bates | |
| 4,935,339 A | 6/1990 | Zahradnik | |
| 7,807,401 B2 | 10/2010 | Kobold et al. | |
| 7,964,363 B2 | 6/2011 | Armbruster et al. | |
| 10,073,103 B1 * | 9/2018 | Noyes | G01N 33/82 |
| 2004/0132104 A1 | 7/2004 | Sackrison et al. | |
| 2013/0295593 A1 | 11/2013 | Beckert et al. | |

FOREIGN PATENT DOCUMENTS

| | | |
|---|---|---|
| EP | 2126586 B1 | 6/2010 |
| WO | 03023391 A | 3/2003 |
| WO | 2012129650 A | 10/2012 |
| WO | 2013081461 A | 6/2013 |

OTHER PUBLICATIONS

Sigma (Pepsin from porcine gastric mucosa) ARO 9/02, pp. 1-2.*
Arnaud et al., Affinity differences for vitamin D metabolites associated with the genetic isoforms of the human serum carrier protein (DBP). Human Genetics 92:183-188 (1993).
Arneson et al. Current Methods for Routine Clinical Laboratory Testing of Vitamin D Levels. Lab Medicine. Winter 2013, vol. 44, No. 1.
Binkley et al., Assay variation confounds the diagnosis of hypovitaminosis D: a call for standardization. J Clin Endocrinol Metab 89:3152-3157 (2004).
Carter, et al. How accurate are assays for 25-hydroxyvitamin D? Data from the international vitamin D external quality assessment scheme. Clinical Chemistry 50(11):2195-2197 (2004).
Hollis et al., Comparison of commercially available (125)I-based RIA methods for the determination of circulating 25-hydroxyvitamin D. Clinical Chemistry 46(10):1657-1661 (2000).
Hollis, et al. Determination of vitamin D status by radioimmunoassay with an 125I-labeled tracer. Clinical Chemistry 39(3):529-533 (1993).
Lensmeyer et al., HPLC method for 25-hydroxyvitamin D measurement: comparison with contemporary assays. Clinical Chemistry 52(6):1120-1126 (2006).
Leventis, et al. Underestimation of serum 25-hydroxyvitamin D by the Nichols Advantage Assay in patients receiving vitamin D replacement therapy. Clinical Chemistry 51(6): 1072-1074 (2005.
Notice of Allowance dated Apr. 25, 2017 for U.S. Appl. No. 14/819,259.
Notice of Allowance dated May 22, 2015 for U.S. Appl. No. 14/203,239.
Notice of Allowance dated Apr. 14, 2015 for U.S. Appl. No. 14/203,206.
Richter et al. Mechanism of activation of the gastric aspartic proteinases: pepsinogen, progastricsin and prochymosin. Biochem. J. (1998) 335, 481-490.
Roth et al., Accuracy and clinical implications of seven 25-hydroxyvitamin D methods compared with liquid chromatography-tandem mass spectrometry as a reference. Annals of Clinical Biochemistry 45(2):153-159 (2008) (Abstract only).
Siemens White Paper "A True Assessment of Total Vitamin D" © 2011 Siemens Healthcare Diagnostics, Inc. Accessed on Jun. 2, 2014 at: http://usa.healthcare.siemens.com/clinical-specialities/bone-metabolism/additional-resources.
Souberbielle et al., Assay-specific decision limits for two new automated parathyroid hormone and 25-hydroxyvitamin D assays. Clinical Chemistry 51(2): 395-400 (2005).
Terry et al., Measurement of 25-hydroxyvitamin D by the Nichols Advantage, DiaSorin Liaison, DiaSorin RIA, and liquid chromatography-tandem mass spectrometry. Clinical Chemistry 51(8):1565-1566 (2005).

(Continued)

*Primary Examiner* — Lisa V Cook

(57) ABSTRACT

Assays for rapid measurement of total vitamin D in blood are provided. Vitamin D is measured following the rapid and irreversible release of vitamin D due to denaturation and digestion of vitamin D binding proteins by aspartyl peptidases (e.g., pepsin) under acidic conditions. Such measurements may be made using a vitamin D binder (e.g., an antibody) to measure competition between free vitamin D and added, labeled vitamin D. Synergy between denaturation and degradation is believed to provide more rapid and more complete release of vitamin D than would occur with acid or enzyme alone.

16 Claims, 5 Drawing Sheets

(56) References Cited

OTHER PUBLICATIONS

U.S. Appl. No. 14/203,206, filed Mar. 10, 2014. Inventor: Tina Noyes.
U.S. Appl. No. 14/203,239, filed Mar. 10, 2014. Inventor: Tina Noyes.
Wootton, Improving the measurement of 25-hydroxyvitamin D. The Clinical Biochemist Reviews 26:33-36 (2005).

\* cited by examiner

RAPID MEASUREMENT OF TOTAL VITAMIN D IN BLOOD

CROSS REFERENCE TO RELATED APPLICATIONS

This Application claims the benefit of priority to U.S. patent application Ser. No. 15/658,920, filed Jul. 25, 2017, now U.S. Pat. No. 10,073,103 which is a continuation of U.S. patent application Ser. No. 14/819,259, filed Aug. 5, 2015, now abandoned and a continuation of U.S. patent application Ser. No. 14/203,239, filed Mar. 10, 2014, now abandoned and claims priority from U.S. Provisional Application No. 61/776,641, filed Mar. 11, 2013.

BACKGROUND

Measurement of small molecule analytes present in blood samples is important for understanding the health status of a subject; however, many small molecules are bound by blood proteins and other molecules that interfere with such measurements. Enzymes have been used in attempts to free target analytes from binding proteins; for example, Bates used pepsin treatment (at pH 1) to free thyroxine from serum proteins for radioimmunoassay measurements in serum following centrifugation of an acid-treated sample (U.S. Pat. No. 3,962,039). However, such harsh treatment of a sample and the use of radioactive tracers to identify analytes are problematic.

Vitamin D is a steroid vitamin essential for normal calcium homeostasis, and thus important, for example, in bone health. Vitamin D comes in many forms; e.g., vitamin D1 through vitamin D5. Two forms of vitamin D are important in humans: vitamin D2 (ergocalciferol) and vitamin D3 (cholecalciferol). In addition to these forms of vitamin D, hydroxy forms of the vitamin may also be found circulating in the blood of a human subject; for example, common hydroxyl forms of vitamin D2 include 25-hydroxy vitamin D2 and 1,25-dihydroxy vitamin D2. Common hydroxyl forms of vitamin D3 include 25-hydroxy vitamin D3 and 1,25-dihydroxy vitamin D3. The major circulating forms of vitamin D in blood are the 25-hydroxyl forms of vitamin D (25-hydroxy vitamin D3 and 25-hydroxy vitamin D2).

Vitamin D3 is formed in the skin from its precursor 7-dehydrocholesterol after ultraviolet irradiation or is absorbed from the diet. It is further hydroxylated in the liver to 25-hydroxy vitamin D3 as the first step of its conversion in the kidney to 1,25-dihydroxyvitamin D3, which is the biologically active form. 25-hydroxy vitamin D3 is the main circulating form of vitamin D, but 25-hydroxy vitamin D2 is also found especially in subjects who take certain vitamin supplements. So it is important to measure both forms of 25-hydroxyvitamin D when monitoring vitamin D status and the effect of vitamin D2 supplementation on vitamin D status. Vitamin-D (in all its isoforms) is bound tightly to Vitamin-D binding protein (VDBP) in blood. In order to measure vitamin D levels in blood, it has to be extracted or displaced from the binding protein. Extraction methods are typically slow and cumbersome.

Armbruster et al. (U.S. Pat. No. 7,964,363) discuss a method for measuring vitamin D levels in a blood sample at neutral pH using a serine protease with endo- and exoproteolytic activity (e.g., proteinase K, Enzyme Commission (EC) number EC 3.4.21.64) in order to digest vitamin D binding proteins in blood plasma or serum; the serine protease is inactivated by addition of a dilution buffer, which allows subsequent use of a monoclonal antibody in determining vitamin D from the serum or plasma sample. However, dilution will reduce the concentration of the protease, rather than inactivate the protease, or may require excessive dilution which also dilutes the sample and the analyte, rendering measurement of the analyte more difficult.

A method for measuring blood levels of vitamin D that has become standard is a radioimmunoassay (RIA) method using a $^{125}$I-labeled vitamin D tracer (Hollis et al., *Clinical Chemistry* 39:529-533 (1993)), available commercially as the DiaSorin RIA33 test using methods and equipment from Diasorin Corporation (Stillwater, Minn.). This RIA method uses acetonitrile extraction followed by competitive radioimmunoassay using $^{125}$I-labelled 25-hydroxy vitamin D and an antibody to 25-hydroxy vitamin D. A second antibody is used as precipitating agent. A different assay, the Diasorin Liaison® test, which does not use radioactive tracers was also developed by the Diasorin Corporation. The Diasorin Liaison® test is a chemiluminescent assay in which serum is incubated with antivitamin-D coated microparticles and isoluminol derivative-conjugated 25-hydroxy vitamin D before measurement of the chemiluminescent signal. Other common vitamin D assays include the IDS Gamma-B assay (which also uses acetonitrile extraction to release vitamin D for detection by antibodies) (ImmunoDiagnostic Systems (IDS) Ltd., Scottsdale, Ariz., USA), and the Nichols Advantage assay (which uses a denaturing agent to separate 25-hydroxy vitamin D from its binding protein) (Nichols Institute Diagnostics, San Clement, Calif.).

However, comparisons of various vitamin D assays, including separate measurements of vitamin D2 and vitamin D3, indicate that the results obtained by different methodologies, and in some cases, by different laboratories, do not always agree (Binkley et al., *J Clin Endocrinol Metab* 89:3152-3157 (2004); Hollis, *Clinical Chemistry* 46(10): 1657-1661 (2000); Lensmeyer et al., *Clinical Chemistry* 52(6):1120-1126 (2006)). For example, reports have been published suggesting that the Nichols Advantage assay is unable to measure samples containing substantial amounts of 25-hydroxy vitamin D2 reliably (Carter et al., *Clinical Chemistry* 50(11):2195-2197 (2004); Terry et al., *Clinical Chemistry* 51(8):1565-1566 (2005)).

Vitamin-D deficiency is associated with bone disease. In its extreme form when left untreated in children the deficiency leads to osteomalacia or rickets, a severe chronic and irreversible condition. Vitamin D supplements provide benefits in the form of enhanced bone health and decreased mortality in elderly women taking such supplements. However, excess vitamin D may cause toxicity; thus, it is believed that vitamin D levels should be maintained, for example, between about 25 ng/milliliter to about 75 ng/milliliter of blood serum. Measurements of vitamin D are needed in order to identify abnormal vitamin D levels in a patient and to confirm response to therapy and the proper maintenance of normal levels.

Thus, it would be beneficial to be able to make rapid measurements of vitamin D in a sample of blood from a subject.

INCORPORATION BY REFERENCE

All patents, patent applications, and publications mentioned herein are hereby incorporated by reference in their entireties.

SUMMARY

Applicants disclose assay methods and compositions useful for such methods suitable for rapid measurement of vitamin D in blood without the use of radioactive isotopes, and without need for extremely harsh acidic conditions. As disclosed herein, such assay methods do not require centrifugation. These methods may be performed using only small amounts of blood, reducing cost of the analysis and reducing discomfort to the subject. For example, the methods disclosed herein may be used to measure vitamin D in blood obtained from a drop, or two drops, or a few drops of blood obtained from a finger-stick, or from a small (e.g., less than about 100 μL, or less than about 50 μL) amount of blood obtained from a vein or artery of a subject. In embodiments, assay methods disclosed herein are effective for determining the total concentration of 25-hydroxyvitamin D3 and 25-hydroxyvitamin D2 in samples of whole blood, blood plasma, or blood serum, with a reportable range of about 5 ng/mL to about 150 ng/mL. These methods are suitable for use in automated devices, further reducing cost and increasing availability of these tests to subjects and increasing their ease of use. Reagents, kits, devices, and systems for these assays are disclosed.

Applicants disclose vitamin D assays and methods using acidic assay conditions and aspartyl peptidases for measurement of vitamin D in blood. Use of aspartyl peptidases under acidic conditions to denature and digest vitamin-D binding proteins (VDBPs) and other proteins, allows the rapid and irreversible release of vitamin D in a sample, effective to allow the detection of, and quantification of, vitamin D in the sample. The synergy between denaturation and degradation of VDBP is believed to provide greater, more rapid, and more complete vitamin D release than would be possible with either condition alone. This enables the release of vitamin D to occur in a short time, so that no pre-treatment period, or only a short pre-treatment period, is needed in the assays disclosed herein. In embodiments, the aspartyl peptidase is pepsin. Following denaturation and digestion under acidic conditions (e.g., about pH 2 to about pH 6), the amount of vitamin D in the sample is measured. In embodiments, such measurements are made under neutral conditions. In embodiments, such measurements comprise binding measurements utilizing labeled vitamin D. For example, competition between exogenously added, labeled vitamin D and free vitamin D from a sample may be used to measure the amount of vitamin D present in a blood sample. Interference by VDBPs is reduced or prevented by the enzymatic degradation of these proteins, so that competition assays disclosed herein are more sensitive and accurate than would be otherwise possible in the absence of such degradation.

Any aspartyl peptidase active at low pH is suitable for the practice of methods disclosed herein. For example, pepsin is a suitable aspartyl peptidase. In embodiments of methods disclosed herein, an aspartyl peptidase active at low pH may be selected from pepsin, cathepsin, renin, chymosin, HIV protease, plasmepsin, retropepsin, and nepenthesin. In embodiments of the methods disclosed herein, the aspartyl peptidase active at low pH comprises pepsin. In embodiments of the methods disclosed herein, a low pH comprises a pH of about pH 5 or less. In embodiments of the methods disclosed herein, a low pH may comprise a pH of about pH 3 or less. In embodiments of the methods disclosed herein, a low pH may comprise a pH of about pH 2 to about pH 6. In embodiments of the methods disclosed herein, a low pH may comprise a pH of about pH 2.5 to about pH 5.5. In embodiments of the methods disclosed herein, a low pH may comprise a pH of about pH 3 to about pH 5. In embodiments of the methods disclosed herein, a low pH may comprise a pH of about pH 2.5 to about pH 4.

Accordingly, Applicants disclose methods for determining the amount of vitamin D in a blood sample, wherein said blood sample comprises vitamin D and a vitamin D binding protein, the methods comprising:

Contacting said blood sample with a low pH composition comprising an aspartyl peptidase active at low pH, whereby a low pH diluted blood sample composition is formed, effective to at least partially denature and at least partially digest said vitamin D binding protein; and Measuring the amount of said vitamin D in said blood sample. A blood sample may comprise whole blood, blood plasma, blood serum, or other form of blood sample. In embodiments of the methods disclosed herein, measuring the amount of vitamin D in a blood sample comprises a competition assay measurement. In embodiments, the low pH composition comprises a buffered low pH composition comprising an aspartyl peptidase active at low pH and a buffer, wherein the buffer provides a pH of between about pH 2 and about pH 6, or between about pH 2.5 and about pH 5.5, or between about pH 3 and about pH 5, or between about pH 2.5 and about pH 4. In embodiments, the low pH composition comprises a buffered low pH composition comprising an aspartyl peptidase active at low pH and a citrate buffer, wherein the citrate buffer provides a pH of between about pH 2 and about pH 6, or between about pH 2.5 and about pH 5.5, or between about pH 3 and about pH 5, or between about pH 2.5 and about pH 4.

Applicants disclose embodiments of methods for determining the amount of vitamin D in a blood sample, wherein said blood sample comprises vitamin D and a vitamin D binding protein, the methods comprising:

Contacting said blood sample with a low pH composition comprising an aspartyl peptidase active at low pH, whereby a low pH diluted blood sample composition is formed, effective to at least partially denature and at least partially digest said vitamin D binding protein;

Contacting said low pH diluted blood sample composition with a neutral pH composition comprising a neutral pH buffer, whereby a neutral pH diluted blood sample composition is formed, effective that said aspartyl peptidase is inactivated; and Measuring the amount of said vitamin D in said blood sample.

In embodiments, the low pH composition comprises a buffered low pH composition comprising an aspartyl peptidase active at low pH and a buffer, wherein the buffer provides a pH of between about pH 2 and about pH 6, or between about pH 2.5 and about pH 5.5, or between about pH 3 and about pH 5, or between about pH 2.5 and about pH 4. In embodiments, the low pH composition comprises a buffered low pH composition comprising an aspartyl peptidase active at low pH and a citrate buffer, wherein the citrate buffer provides a pH of between about pH 2 and about pH 6, or between about pH 2.5 and about pH 5.5, or between about pH 3 and about pH 5, or between about pH 2.5 and about pH 4.

Applicants disclose further methods for determining the amount of vitamin D in a blood sample, wherein said blood sample comprises vitamin D and a vitamin D binding protein, the methods comprising:

Contacting said blood sample with a low pH composition comprising an aspartyl peptidase active at low pH, whereby a low pH diluted blood sample composition is formed, effective to at least partially denature and at least partially digest said vitamin D binding protein;

Contacting said low pH diluted blood sample composition with a neutral pH composition comprising a neutral pH buffer, whereby a neutral pH diluted blood sample composition is formed, effective that said aspartyl peptidase is inactivated;

Contacting said neutral pH diluted blood sample composition with a vitamin D binder; and Measuring the amount of said vitamin D in said blood sample.

In embodiments, the low pH composition comprises a buffered low pH composition comprising an aspartyl peptidase active at low pH and a buffer, wherein the buffer provides a pH of between about pH 2 and about pH 6, or between about pH 2.5 and about pH 5.5, or between about pH 3 and about pH 5, or between about pH 2.5 and about pH 4. In embodiments, the low pH composition comprises a buffered low pH composition comprising an aspartyl peptidase active at low pH and a citrate buffer, wherein the citrate buffer provides a pH of between about pH 2 and about pH 6, or between about pH 2.5 and about pH 5.5, or between about pH 3 and about pH 5, or between about pH 2.5 and about pH 4.

In embodiments, a vitamin D binder may be an anti-vitamin D antibody. In embodiments, more than one type of vitamin D binder may contact the neutral pH diluted blood sample composition. In embodiments comprising more than one type of vitamin D binder, a neutral pH diluted blood sample composition may be contacted with a plurality of types of vitamin D binders that may comprise one, two or more types of anti-vitamin D antibodies and/or other compounds which bind vitamin D.

Applicants also disclose further embodiments of methods as discussed above, which comprise further steps, including steps wherein measuring the amount of said vitamin D in said blood sample comprises:

Adding labeled vitamin D to said neutral pH diluted blood sample composition comprising an anti-vitamin D antibody;

Contacting said neutral pH diluted blood sample composition comprising an anti-vitamin D antibody with a capture surface, wherein said capture surface comprises capture elements configured to bind to said anti-vitamin D antibody; and Detecting said labeled vitamin D, wherein the amount of detected vitamin D provides a measure of the amount of vitamin D present in the blood sample.

Applicants also disclose herein embodiments of methods as discussed above, and which further comprise a washing step prior to said step of measuring the amount of vitamin D. Applicants also disclose herein embodiments of methods as discussed above, and which further comprise a washing step prior to said step of detecting labeled vitamin D. In embodiments, such a washing step may be effective to remove unbound labeled vitamin D.

In embodiments of the methods disclosed herein, said labeled vitamin D may comprise a label selected from a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, a quencher, and derivatives thereof. In embodiments, labeled vitamin D comprises an alkaline phosphatase label or a horseradish peroxidase label.

In embodiments of the methods disclosed herein, determination of the amount of vitamin D present in the blood sample may comprise use of a competition measurement, e.g., a measurement made in a competition assay. In embodiments of the methods disclosed herein, determination of the amount of vitamin D present in the blood sample comprises comparison of the amount of labeled vitamin D detected with a standard curve obtained from control vitamin D competition assays. In embodiments, determination of the amount of vitamin D present in the blood sample may comprise use of a radioimmunoassay, may comprise use of chromatography, or may comprise use of spectrophotometry.

In embodiments of the methods disclosed herein, capture elements configured to bind to a vitamin D binder, such as an anti-vitamin D antibody, may be selected from a polynucleotide, a polypeptide, a peptide nucleic acid, a locked nucleic acid, an oligosaccharide, a polysaccharide, an antibody, an antibody fragment, an antibody mimic, an immunoadhesin, a receptor, a ligand, biotin, avidin, streptavidin, Extravidin, neutravidin, other avidin derivative or avidin analog, a metal, an epitope tag, and any portion of any of these. In embodiments of the methods disclosed herein, capture elements configured to bind to said anti-vitamin D antibody comprise avidin, streptavidin, or biotin.

Vitamin D may take one or more of several different forms. The naturally occurring form of 25-hydroxy vitamin D is the D3 form; however some vitamin supplements contain 25-hydroxy vitamin D2 and therefore detection of the D2 form, as well as the D3 form, is also useful (e.g., individuals taking vitamin D2 supplements may be at risk for toxicity if vitamin D2 levels are not monitored). In embodiments of the methods disclosed herein, vitamin D comprises one or more of vitamin D2; vitamin D3; 25-hydroxy vitamin D2; 25-hydroxy vitamin D3; 1,25-dihydroxy vitamin D2; and 1,25-dihydroxy vitamin D3. In embodiments of the methods disclosed herein, and of reagents useful in these methods, more than one type of vitamin D binder may be provided in a reagent. For example, a type of vitamin D binder may have a binding affinity for vitamin D2 and may have another binding affinity for vitamin D3, or for 25-hydroxy vitamin D2; or for 25-hydroxy vitamin D3; or for 1,25-dihydroxy vitamin D2; or for 1,25-dihydroxy vitamin D3. Such binding affinities may be the same, or may differ from each other. In embodiments, a reagent for use in the methods disclosed herein may include more than one type of vitamin D binder, each of which type of vitamin D binder may bind more than one form of vitamin D. For example, a reagent for use in the methods disclosed herein may comprise two types of vitamin D binders, each of which binds two forms of vitamin D. In embodiments of such reagents, the relative amounts of the types of vitamin D binders may be selected so that the total (combined) binding affinity of the two types of binders for one form of vitamin D is equal to, or substantially equal to, the total (combined) binding affinity of the two types of binders for the other form of vitamin D. In embodiments, an anti-vitamin D antibody is a type of vitamin D binder, and a different anti-vitamin D antibody is a different type of vitamin D binder.

For example, where a first type of vitamin D binder binds to both vitamin D2 and to vitamin D3, having a first vitamin D2 binding affinity and a second vitamin D3 affinity, and where a second type of vitamin D binder binds to both vitamin D2 and to vitamin D3, having a second vitamin D2 binding affinity and a second vitamin D3 affinity, and wherein one or both of (i) said first vitamin D2 binding affinity differs from said second vitamin D2 binding affinity, and (ii) said first vitamin D3 binding affinity differs from said second vitamin D3 binding affinity, effective that the first type of vitamin D binder and the second type of vitamin D binder together provide a combined vitamin D2 binding affinity and a combined vitamin D3 binding affinity; Applicants disclose a reagent comprising a first type of vitamin D binder at a first concentration and a second type of vitamin D binder at a second concentration, wherein the ratio of said first concentration to said second concentration is a ratio effective that said combined vitamin D2 binding affinity is similar to said combined vitamin D3 binding affinity. Applicants further disclose methods, as discussed herein, for determining vitamin D in a sample of whole blood, blood plasma, or blood serum, using a reagent comprising the first type of vitamin D binder at a first concentration and the second type of vitamin D binder at a second concentration, wherein the ratio of said first concentration to said second concentration is a ratio effective that said combined vitamin D2 binding affinity is similar to said combined vitamin D3 binding affinity.

In embodiments of reagents comprising a first type of vitamin D binder at a first concentration and a second type of vitamin D binder at a second concentration, and in embodiments of methods using such reagents, the ratio of said first concentration to said second concentration is a ratio effective that said combined vitamin D2 binding affinity is substantially equal to said combined vitamin D3 binding affinity.

In embodiments of the methods and of the reagents disclosed herein, one or more of the types of vitamin D binders in such reagents comprise a type of an anti-vitamin D antibody. In embodiments of the methods and of the reagents disclosed herein, two or more of the types of vitamin D binders in such reagents comprise types of anti-vitamin D antibodies.

In embodiments of the methods disclosed herein, a blood sample may have a volume of less than about 100 μL, or less than about 50 μL, or less than about 25 μL, or less than about 10 μL. In embodiments, a blood sample may be obtained by a finger-stick, and the amount of blood may be an amount obtainable by a finger-stick. In embodiments, the blood sample may be obtained by use of a capillary tube or other sampling device. In embodiments of the methods disclosed herein, determination of the amount of vitamin D in a blood sample may be performed in less than about one hour, or, in embodiments, in less than about 40 minutes, or in less than about 30 minutes, after contacting said blood sample with a low pH composition comprising an aspartyl peptidase active at low pH. A blood sample may be diluted with a diluent prior to, or during, the course of the analysis of the vitamin D level in the blood sample.

The assays disclosed herein may be performed on a device, or on a system, for processing a sample. The assays disclosed herein can be readily incorporated into and used in an automated assay device, and in an automated assay system. For example, systems as disclosed herein may include a communication assembly for transmitting or receiving a protocol based on the analyte to be detected (e.g., vitamin D) or based on other analytes to be detected by the device or system. In embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Accordingly, Applicants disclose devices configured to measure vitamin D in a sample of blood according to a method disclosed herein. Devices configured to measure vitamin D in a sample of blood according to a method disclosed herein may be configured to determine vitamin D from a sample of blood that comprises no more than about 100 μL of blood, or no more than about 50 μL of blood, or, in embodiments, wherein said sample of blood comprises no more than about 25 μL of blood, or wherein said sample of blood comprises no more than about 10 μL of blood. Such devices may be configured to measure vitamin D in a sample of blood in less than about one hour, or, in embodiments, in less than about 40 minutes, or in less than about 30 minutes.

Devices disclosed herein may be configured to perform an assay for the measurement of vitamin D and also to perform an assay for the measurement of another analyte in the blood sample. Devices disclosed herein may be configured to perform an assay for the measurement of vitamin D and also to perform an assay comprising the measurement of a morphological characteristic of a blood cell in the blood sample. Devices disclosed herein may be configured to perform an assay for the measurement of vitamin D and also to perform an assay comprising the measurement of another blood analyte, e.g., another analyte relevant to the management of the calcium status of a subject. Such devices may be configured wherein the assays, or the order of performance of assays, that are performed by said device may be altered by communication with another device.

Applicants also disclose systems comprising a device as disclosed herein. In embodiments, the system comprises a device that is configured to perform an assay for the measurement of vitamin D and also to perform an assay for the measurement of another analyte in the blood sample. In embodiments, the system comprises a device that is configured to perform an assay for the measurement of vitamin D and also to perform an assay for the measurement of a morphological characteristic of a blood cell in the blood sample. In embodiments of such a system, assays, or the order of performance of assays, that are performed by said device may be altered by communication with another device.

Applicants also disclose reagents for use in a method of measuring vitamin D disclosed herein, the reagents comprising an aspartyl peptidase and having a pH of between about pH 2 and about pH 5. In embodiments, the aspartyl peptidase is selected from pepsin, cathepsin, renin, chymosin, HIV protease, plasmepsin, retropepsin, and nepenthesin. In embodiments, the aspartyl peptidase comprises pepsin, and may comprise porcine gastric pepsin. In embodiments, the reagent has a pH of about pH 5 or less. In embodiments, the reagent has a pH of about pH 3 or less. In embodiments, the reagent comprises a buffered low pH composition comprising an aspartyl peptidase active at low pH and a buffer, wherein the buffer provides a pH of between about pH 2 and about pH 6, or between about pH 2.5 and about pH 5.5, or between about pH 3 and about pH 5, or between about pH 2.5 and about pH 4. In embodiments, the reagent comprises a buffered low pH composition comprising an aspartyl peptidase active at low pH and a citrate buffer, wherein the citrate buffer provides a pH of between about pH 2 and about pH 6, or between about pH 2.5 and about pH 5.5, or between about pH 3 and about pH 5, or between about pH 2.5 and about pH 4.

Applicants disclose reagents for use in a method of measuring vitamin D, comprising binders of vitamin D. For example, a vitamin D binder may be an anti-vitamin D antibody. In embodiments, a vitamin D binder may be any compound, including a polypeptide compound, or a non-polypeptide compound, which selectively binds vitamin D. In embodiments, a vitamin D binder may bind more than one form of vitamin D. In embodiments, a vitamin D binder that binds more than one form of vitamin D may bind a first form of vitamin D with a higher affinity than the affinity with which it binds a second form of vitamin D. In embodiments, a reagent may comprise a vitamin D binder that binds a first form of vitamin D about twice as well as it binds a second form of vitamin D, or may bind a first form of vitamin D about three times as well as it binds a second form of vitamin D, or may bind a first form of vitamin D many times as well as it binds a second form of vitamin D.

Applicants disclose reagents for use in a method of measuring vitamin D, comprising a first anti-vitamin D antibody and a second anti-vitamin D antibody, wherein each of said anti-vitamin D antibodies bind both vitamin D2 and vitamin D3 with vitamin D2 binding affinities and with vitamin D3 affinities, respectively, and wherein one or both of: (i) the vitamin D2 binding affinity of said first vitamin D antibody differs from the vitamin D2 binding affinity of said second vitamin D antibody, and (ii) the vitamin D3 binding affinity of said first vitamin D antibody differs from the vitamin D3 binding affinity of said second vitamin D antibody, effective that said first and said second anti-vitamin D antibodies provide a combined vitamin D2 binding affinity and a combined vitamin D3 binding affinity, said reagent comprising the first anti-vitamin D antibody at a first concentration and the second anti-vitamin D antibody at a second concentration, wherein the ratio of said first concentration to said second concentration is a ratio effective that the combined vitamin D2 binding affinity is equal to the combined vitamin D3 binding affinity. In embodiments, the concentration of a first antibody may be about twice the concentration of a second antibody. In embodiments, the reagent may comprise about 100 ng/ml of a first antibody and may comprise about 50 ng/ml of a second antibody. In embodiments, the reagent may have a pH of between about pH 7.5 and about pH 8.5.

Applicants disclose kits for use in a method of measuring vitamin D in a sample of blood, comprising a reagent as disclosed herein, and a container. In embodiments, a container of a kit disclosed herein may comprise a septum, barrier, cap, or closure effective to prevent evaporation or aerosolization of the reagent. Such prevention of evaporation or aerosolization of the reagent may be effective to prevent reagent loss, e.g., over time, due to spillage, or for other reasons. Such a septum, barrier, cap, or closure may be effective to prevent contamination of the reagent or to prevent contamination of a device in which the container is disposed. In embodiments, a kit for use in a method of measuring vitamin D in a sample of blood comprises a reagent as disclosed herein, and instructions for its use in an assay disclosed herein.

Assays, methods, reagents, kits, devices, and systems as disclosed herein provide advantages over prior assays, methods, reagents, kits, and systems by allowing the rapid and inexpensive measurement of vitamin D, including vitamin D sub-fractions in a single assay. By avoiding the extremely harsh conditions of pH 1, e.g., using buffered solutions, such as citrate buffered solutions at about pH 2 to about pH 6, or at about pH 2.5 to about pH 4, while allowing use of aspartyl peptidases active at low pH, proteins are denatured and digested without substantial precipitation, allowing the use of optical detection methods, such as detection of chemiluminescence, luminescence, fluorescence, turbidity, absorbance, or other optical methods—and maintaining compatibility with fluid transfer methods using pipettes or other microfluidic means, and so obviating the need for centrifugation. Detection by luminescence, chemiluminescence, fluorescence, turbidity, absorbance, or other optical methods, allows for avoiding the use of radioactive isotopes for detection of vitamin D. Use of buffered low pH solutions, such as citrate-buffered low pH solutions, provides a consistent final pH following mixing with different clinical samples, allowing for consistent and reliable assay results.

The methods and assays disclosed herein allow for measurement of vitamin D and one or more other analytes from the same sample of blood, or from the same portion of a sample of blood. Providing desired measurements in a single assay simplifies procedures, reduces likelihood of error, reduces variability of results, and allows for more rapid and more inexpensive procedures. Accordingly, the assays, methods, reagents, kits, devices, and systems disclosed herein provide improvements over the art.

Applicants disclose assay methods for determining vitamin D in plasma, or serum, or in whole blood. The assay methods disclosed herein were found to perform well with samples of whole blood, plasma and serum. Applicants are not aware of any other vitamin D test method able to measure vitamin D in whole blood. Accordingly, the assay methods disclosed in the present application provide advantages and capabilities not available from prior methods.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
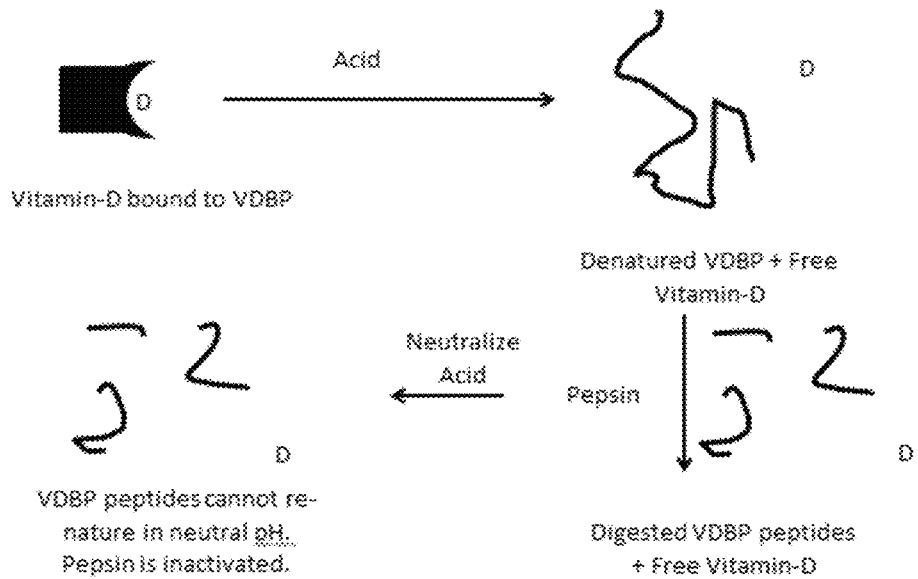
FIG. 1 provides a schematic of an embodiment of the sample pretreatment method. In the figure, "D" represents vitamin D, shown bound to vitamin D binding protein (VDBP) in the upper left of the figure, and shown free of VDBP elsewhere in the figure.
Figure 2:
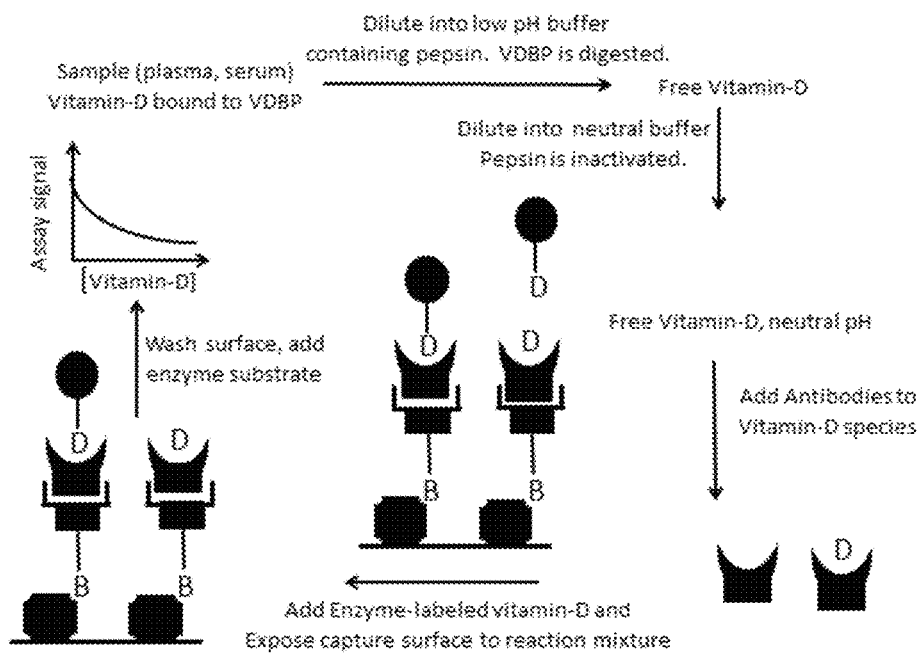
FIG. 2 presents an immunoassay method embodiment which uses the pretreatment method. In the figure, "D" represents vitamin D, which may be free vitamin D as noted in the figure, and which is shown as vitamin D bound to anti-vitamin D antibody and as labeled vitamin D; and "B" represents biotin (part of a biotin-labeled anti-sheep antibody).
Figure 3:
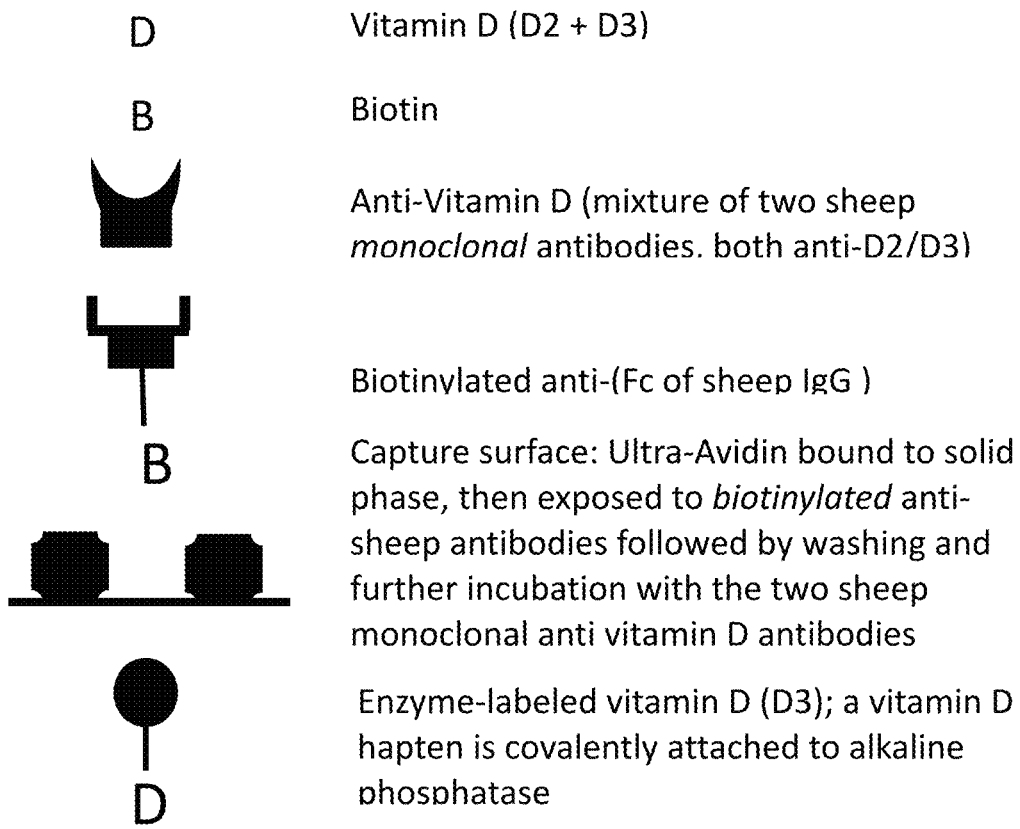
FIG. 3 provides a key to the assay reagents as illustrated in FIGS. 1 and 2.

Applicants disclose assays in which a proteolytic enzyme active under acidic condition, such as an aspartyl peptidase, is used to release vitamin-D and to digest vitamin-D binding protein (VDBP) and other proteins in acid conditions. Such other proteins include, for example, other proteins (such as albumin) which may bind vitamin D, DNAases, RNAases, and other proteins. The use of an apartyl peptidase under acidic conditions effective to at least partially denature and at least partially digest VDBP enables the release of vitamin D to occur in a short time, so that no pre-treatment period, or only a short pre-treatment period, is needed in the assays disclosed herein. Aspartyl peptidases (E.C. 3.4.23) include pepsin, cathepsin, renin, chymosin, HIV protease, plasmepsin, retropepsin, and nepenthesin, and are most active at acidic pH (e.g., about pH 2 to 6, or about pH 3 to 5). Pepsin is an aspartyl peptidase that is well-suited for this purpose because pepsin acts only in acid conditions which denature the target protein rendering it more ready for proteolytic attack. In embodiments, the aspartyl peptidase is a pepsin selected from porcine pepsin, bovine pepsin, ovine pepsin, murine pepsin, and human pepsin. In embodiments, the aspartyl peptidase is a cathepsin selected from cathepsin A, cathepsin B, cathepsin C, cathepsin D, cathepsin E, cathepsin F, and cathepsin G. In embodiments, the aspartyl peptidase is a renin selected from porcine renin, bovine renin, ovine renin, murine renin, and human renin. In embodiments, the aspartyl peptidase is a chymosin selected from porcine chymosin, bovine chymosin, ovine chymosin, murine chymosin, and human chymosin. In embodiments, the aspartyl peptidase is HIV protease. In embodiments, the aspartyl peptidase is a plasmepsin selected from porcine plasmepsin, bovine plasmepsin, ovine plasmepsin, murine plasmepsin, and human plasmepsin. In embodiments, the aspartyl peptidase is a nepenthesin selected from porcine nepenthesin, bovine nepenthesin, ovine nepenthesin, murine nepenthesin, and human nepenthesin.

Use of buffered solutions, such as citrate buffered solutions, stabilizes the pH at a desired low pH, providing stable conditions for reliable and repeatable assay conditions. Such stability is not believed to be possible, for example, from solutions merely containing high concentrations of HCl or other strong acid, which produced turbid or opaque conditions unsuitable for optical measurements such as luminescence, chemiluminescence, fluorescence, turbidity, absorbance or other optical measurements. Citrate buffer was found to provide better results than acid addition alone, and allowed milder assay conditions (e.g., about pH 2.5 to about pH 4) than obtained with unbuffered strong acid. Use of buffered solutions, such as citrate buffer, was found to provide accurate and reliable assays. The citrate buffer seemed more effective overall at separating the target from the VDBP, and also was able to produce a consistent final pH after mixing with different clinical samples.

Following inactivation and digestion of VDBP by the aspartyl peptidase active at low pH, effective to release vitamin D bound to VDBP, detection and/or measurement of vitamin D may be performed at neutral pH, e.g., by antibody-mediated techniques. Enzymatic degradation at acid pH is useful, since acid denaturation alone may not be sufficient to release the vitamin, and since undigested VDBP might re-nature and re-bind the vitamin if the sample is restored to neutral pH without digestion of the VDBP. Further advantages of the methods disclosed herein include use of acid-active enzymes such as pepsin or other aspartyl peptidases, which are inactivated by returning the sample to neutral pH (as may be useful where vitamin D is measured by an immunoassay) and thereafter cannot digest assay reagents such as antibodies or enzymes and the like.

For example, in embodiments of the methods and assays disclosed herein, biotin-labeled anti-sheep antibody coated on UltraAvidin™ was used as a capture surface in a competitive enzyme-linked immunosorbent assay (ELISA). Sample, (serum, plasma, or whole blood) was diluted and mixed with pepsin in a low pH buffer to denature and digest vitamin D binding proteins (VDBPs) and other interfering proteins. The mixture was then further diluted using a pH 8.0 buffer to inactivate the pepsin, and anti-25-hydroxy vitamin D antibodies (typically a mixture of antibodies targeting both 25-hydroxy vitamin D2 and 25-hydroxy vitamin D3) were added. Following a short incubation period (typically 10 minutes), an alkaline-phosphatase-labeled 25-hydroxy vitamin D3 conjugate was added, and the resulting mixture was incubated in contact with the capture surface. The capture surface was then washed and the capture surface contacted with alkaline phosphatase substrate to produce a chemiluminescent signal. The chemiluminescent signal was read to determine the amount of 25-hydroxy vitamin D in the sample. A greater amount of total 25-hydroxy vitamin D in the sample resulted in lower binding of the labeled 25-hydroxy vitamin D3 conjugate to the capture antibody. Thus, the chemiluminescent signal generated by the assay was inversely proportional to the concentration of 25-hydroxy vitamin D in the sample.

The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units.

A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Embodiments of devices and systems for measuring vitamin D in at least a portion of a blood sample; and embodiments of devices and systems for measuring vitamin D in at least a portion of a blood sample, and at least one other biologically relevant attribute from said blood sample from a subject; and description and disclosure of examples of reagents, assays, methods, kits, devices, and systems which may use, or be used with, reagents, assays, methods, kits, devices, and systems disclosed herein may be found, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; and U.S. application Ser. No. 13/244,947, filed Sep. 26, 2011, the disclosures of which patents and patent applications are all hereby incorporated by reference in their entireties.

DEFINITIONS

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. As used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

As used herein, the term "about" refers to an amount that is within about 10% of the amount to which the modifier "about" refers. Thus, for example, the phrase "no more than about 50 µL of blood" refers to an amount of blood that may be no more than 55 µL in volume.

As used herein, the term "similar" when applied to numerical values means that two or more numerical values are close in value to each other, e.g., a first value differs from a second value by no more than about 50% of the first value, or by no more than about 40%, or by no more than about 30%, or by no more than about 20%, or by no more than about 15%. The term "similar" when applied to two non-numerical characteristics means that the two characteristics resemble each other, or share common properties.

As used herein, the term "substantial" means more than a minimal or insignificant amount; and the term "substantially" means more than minimally or insignificantly.

As used herein, the terms "substantially equal" and "substantially the same" when applied to numerical values means that two or more numerical values are very close in value to each other, e.g., a first value differs from a second value by no more than about 10% of the first value, or by no more than about 5%, or by no more than about 3%, or by no more than about 2%, or by no more than about 1%. The terms "substantially equal" and "substantially the same" when applied to two non-numerical characteristics means that the two characteristics differ from one another only in insignificant ways, or are the nearly the same as each other, or are identical.

The terms "blood" and "whole blood" refer to blood as it exists within an animal and as directly obtained from a subject in a blood sample. Blood contains red blood cells, white blood cells, proteins such as albumin, globulins, and clotting factors, salts, water, and other constituents.

The terms "plasma" and "blood plasma" refer to the liquid portion of blood (e.g., a blood sample) that remains after the removal of blood cells. Red blood cells and white blood cells may be removed by centrifugation of a blood sample, leaving plasma above the pelleted cells in the bottom of the centrifuge tube. Plasma retains blood clotting factors, and is obtained from anti-coagulated blood samples.

The terms "serum" and "blood serum" refer to the liquid portion of blood that remains after blood is allowed to clot, and the clot is removed. Serum differs from plasma in that serum lacks clotting factors: since clotting requires fibrin, thrombin, and other proteins, which form and remain part of a blood clot, serum lacks these proteins while plasma contains them.

As used herein, "vitamin D" refers to vitamin D in all its forms, e.g., vitamin D1 through vitamin D5, including without limitation vitamin D2 (ergocalciferol), vitamin D3 (cholecalciferol), and hydroxy forms of vitamin D. The major circulating forms of vitamin D are 25-hydroxy vitamin D3 and 25-hydroxy vitamin D2.

As used herein, the term "Relative Light Units" and its abbreviation "RLU" refer to the units used to scale the output of instruments which measure light intensity (e.g., a photomultiplier tube, luminometer, or other such instrument or device). RLU values are typically proportional to photon number; reporting light intensity in RLU allows comparison between experiments and between instruments.

As used herein, the term "coefficient of variance" and its abbreviations "COV" and "CV" are used as commonly understood in the art; COV values are typically reported as a percent. The COV is calculated by dividing the standard deviation (SD) of a set of experimental values by the mean value (M) of that set of experimental values to obtain the ratio of the standard deviation to the mean, and then multiplying that ratio by 100:

$$COV = SD/M \times 100$$

The COV provides a measure of the differences between observed measurement values where multiple experiments and measurements are made; where multiple experiments give widely varying results, the COV is large; where multiple experiments give results that are all closely matched, the COV is small. A small COV for the results of an experimental procedure indicates that the experimental procedure provides consistent results; this is typically interpreted to mean that a small COV indicates better results than a larger COV.

As used herein, a "binding compound", a "binding molecule" and a "binding protein" all refer to molecules that bind to a target molecule. For example, an antibody or antibody fragment which specifically binds vitamin D2 may be termed a vitamin D2 binding molecule, or a vitamin D2 binder; and an antibody or antibody fragment which specifically binds vitamin D3 may be termed a vitamin D3 binding molecule, or a vitamin D3 binder. In some instances, the same molecule may bind more than one target molecule; this may be true for antibodies and antibody fragments as well as for other binders. Thus, for example, an antibody or antibody fragment which specifically binds vitamin D2 and vitamin D3 (e.g., binds D2 and D3 forms of vitamin D, but does not significantly bind other target molecules that are not forms of vitamin D) may be termed a vitamin D binding molecule; a vitamin D binder; a vitamin D2/D3 binding molecule; a vitamin D2/D3 binder; a vitamin D2 and D3 binding molecule; a vitamin D2 and D3 binder; or other similar term.

As used herein, the term "binder" refers to a binding molecule as discussed above. In particular, a "vitamin D binder" is a compound that specifically binds to vitamin D in any of its forms. A vitamin D binder may be an antibody, an antibody fragment, an aptamer, a binding protein, a receptor, an immunoadhesin, a small molecule having affinity for vitamin D, or any compound that binds to one or more forms of vitamin D.

As used herein, the term "bound" means that two compounds are in a tight, non-covalent, interaction with one another. Each compound is bound to the other. Binding may be specific: for example, when a ligand is in contact with its receptor, the ligand is said to be bound to the receptor, and when an antigen is in contact with an antibody specific for that antigen, the antigen is said to be bound to the antibody. The term "bound" is typically used to refer to specific binding between binding partners. Compounds which bind are said to "associate" with each other, and the rate of binding is the association rate.

As used herein, the term "unbound" refers to a compound that is not in a tight, non-covalent, interaction with another compound. Typically, the term "unbound" refers to the lack of specific binding between potential binding partners. For example, where antigens and antibodies are present in a solution, an antigen molecule that is free in the solution is said to be an unbound antigen. The rate of unbinding is the dissociation rate.

It will be understood that binding between partners may be transient, so that there may be continuous binding and unbinding between compounds that bind each other; however, an equilibrium may be reached where the numbers of bound and unbound compounds remain substantially constant for a period of time.

As used herein, the term "competitive binding" refers to situations where multiple potential binding partners are present in the same solution, where some potential binding partners bind together and others remain free in solution. The multiple binding partners may include a single population of substantially identical compounds (e.g., ligands or antigens) which may bind with a target binding partner (e.g., a receptor or antibody), or may include two or more populations of potential binding partners (e.g., ligands or antigens), each of which population may bind with a target binding partner (e.g., a receptor or antibody). For example, where multiple antigens bind a single antibody, the antigens are said to "cross-react" with the antibody, and may be termed "cross-reactants" with respect to that antibody. In some cases, one population which binds may be labeled, and another population may be unlabeled.

As used herein, the terms "competition assay", "competition methods", "competitive binding assays" and the like refer to assays and methods in which an analyte and a labeled molecule that is believed to be nearly identical, or at least similar, to the analyte (with respect to its binding characteristics) are present in a solution with a molecule which binds both the analyte and the labeled molecule (e.g., an antibody). Competitive binding assays rely on the ability of a labeled molecule (such as, e.g., labeled vitamin D) to compete with the analyte (such as, e.g., vitamin D) for binding with a limited amount of binder (e.g., an antibody, such as an anti-vitamin D antibody). The amount of analyte in the test sample is inversely proportional to the amount of labeled molecule that becomes bound to the molecule which binds both the analyte and the labeled molecule.

Sandwich assays involve the use of two antibodies, each capable of binding to a different immunogenic portion, or epitope, of the analyte to be detected. In a sandwich assay, the test sample analyte is bound by a first antibody which is immobilized on a solid support, and thereafter a second antibody binds to the analyte, thus forming an insoluble three part complex (see, e.g., U.S. Pat. No. 4,376,110). The second antibody may itself be labeled with a detectable moiety (direct sandwich assays), or may be measured using an anti-immunoglobulin antibody that is labeled with a detectable moiety (indirect sandwich assay). For example, one type of sandwich assay is an ELISA assay (enzyme linked immunosorbent assay), in which case the detectable moiety is an enzyme. Useful for detecting proteins and other large target compounds, sandwich ELISA assays are typically not used for the detection of small molecules.

As used herein, the term "antibody" is used in the broadest sense and specifically covers single monoclonal antibodies (including agonist and antagonist antibodies) and antibody compositions with polyepitopic specificity. Thus, antibodies may be polyclonal antibodies, e.g., may be antibodies purified from the blood of an animal such as a sheep or goat which has been challenged by a target antigen, and may be monoclonal antibodies. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222:581-597 (1991), for example. Monoclonal antibodies are obtained from a population of substantially homogeneous antibodies, i.e., the individual antibodies comprising the population are identical except for possible naturally-occurring mutations that may be present in minor amounts.

Antibodies (e.g., IgG antibodies) are usually heterotetrameric glycoproteins of about 150,000 daltons, composed of two identical light chains (LCs) and two identical heavy chains (HCs). Each light chain is linked to a heavy chain by one covalent disulfide bond, while the number of disulfide linkages varies between the heavy chains of different immunoglobulin isotypes. Each heavy and light chain also has regularly spaced intrachain disulfide bridges between cysteines. Each heavy chain has at a variable domain, followed by a number of constant domains. The variable domains are disposed closer to the amino-terminal (N-terminal) portion of the HC than are the constant domains; conversely, the constant domains are disposed closer to the carboxy-terminal (C-terminal) portion of the HC than are the variable domains. Similarly, each light chain has a variable domain at one end (towards the N-terminal) and a constant domain at its other end (towards the C-terminal); the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)). The variable domains form the antigen-binding sites; thus an intact antibody has two antigen binding sites composed of variable domains of the LC and HC pairs.

"Antibody fragment", and all grammatical variants thereof, as used herein are defined as a (1) portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody, and (2) constructs comprising a portion of an intact antibody (as defined by the amino acid sequence of the intact antibody) comprising the antigen binding site or variable region of the intact antibody. Examples of antibody fragments include Fab, Fab', Fab'-SH, F(ab')2, Fd, Fc, Fv, diabodies, and any other "Non-single-chain antigen-binding unit" as described, e.g., in U.S. Pat. No. 7,429,652. The term "intact antibody" refers to the complete antibody, or the amino acid sequence of the complete antibody, of which an antibody fragment is a part. It will be understood that an antibody fragment may be produced by partial digestion (e.g., by papain or pepsin) of an intact antibody, or may be produced by recombinant or other means.

The term "diabodies" refers to small antibody fragments with two antigen-binding sites, which fragments comprise a heavy chain variable domain connected to a light chain variable domain in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

As used herein, an "antigen-binding antibody fragment" is any antibody fragment that retains the ability to bind to the specific target to which the intact antibody specifically binds. An antigen-binding antibody fragment may have different (e.g., lesser) binding affinity for the target antigen than the intact antibody.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222: 581-597 (1991), for example.

A "secondary antibody" is an antibody used to bind other antibodies; these other antibodies are termed primary antibodies. Secondary antibodies may be used, for example, to bind an antigen-binding antibody to a capture surface. For example, where a primary antibody is used to recognize a target antigen, a secondary antibody may be used to bind the primary antibody to a capture surface. Any antibody, from any source, including a polyclonal antibody, a monoclonal antibody, an antibody fragment, an antibody derivative, and combinations of these, may be used as a secondary antibody. In some instances, a primary antibody may be, e.g., a sheep antibody (an antibody raised in sheep), and a secondary antibody may be, e.g., a rabbit antibody (an antibody raised in rabbits).

An "anti-sheep antibody" is an antibody that binds sheep antibodies, typically by recognizing an epitope on the Fc portion of the sheep antibody. For example, in some examples disclosed herein, vitamin D (both labeled and unlabeled) is bound by a sheep antibody; that sheep antibody is itself bound by an "anti-sheep antibody" which recognizes an epitope on the vitamin-D-binding sheep antibody, and (as disclosed herein) such binding may be used to attach the bound vitamin D to a capture surface. The anti-sheep antibodies used in the examples disclosed herein are rabbit polyclonal antibodies raised against the Fc portion of sheep IgG antibodies; however, any antibody, whether polyclonal or monoclonal, rabbit, or other animal, that binds sheep antibodies may be used to bind sheep antibodies to a capture surface.

An antibody that "specifically binds to" or is "specific for" a particular polypeptide or, an epitope on a particular polypeptide is one that binds to that particular polypeptide or epitope on a particular polypeptide without substantially binding to any other polypeptide or polypeptide epitope.

As used herein, the term "aptamer" refers to a nucleic acid molecule capable of binding to a target molecule. The nucleic acid may be a deoxyribonucleic acid, a ribonucleic acid, a linked peptide nucleic acid, or other nucleic acid, analog, or derivative thereof. The generation and use of aptamers is known in the art; see, e.g., U.S. Pat. No. 5,475,096.

An immunoadhesin is an antibody-like chimeric molecule comprising a portion of an antibody (e.g., some or all of the Fc region of an IgG antibody) linked to a receptor or ligand having affinity for a target molecule. Immunoadhesins combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin. Immunoglobulin fusions are discussed, for example, in U.S. Pat. No. 5,428, 130.

As used herein, the term "small molecule" refers to a compound, typically a non-polymeric organic compound, that is smaller than a typical protein. Examples of small molecules include acetylsalicylic acid (aspirin), caffeine, cholesterol, vitamin D, and other molecules.

The terms "antigen", "target molecule", "target polypeptide", "target epitope", and the like are used herein to denote the molecule (or, regarding an epitope, portion of molecule) specifically bound by a binder such as an antibody, antibody fragment, or other binder. For example, vitamin D is the target molecule for an anti-vitamin D antibody or antigen-binding fragment thereof.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

The word "label" or "detectable label" when used herein refer to a detectable compound or composition which is linked (e.g., conjugated) directly or indirectly to a compound so as to generate a "labeled" compound. The label may be detectable by itself (e.g. radioisotope labels or fluorescent labels) or, in the case of an enzymatic label, may catalyze chemical alteration of a substrate compound or composition which is detectable. A label may serve as a substrate for an enzyme, or may otherwise participate in a reaction. A label may aid in binding a compound to another compound or to a substrate. A label may be, for example, selected from the said labeled vitamin D, wherein the amount of detected vitamin D provides a measure of the emiluminescent moiety, an enzymatic label, a magnetic label, a paramagnetic label, a contrast agent, a nanoparticle, a radioisotope, biotin, streptavidin, and a quencher.

For example, a label may be an alkaline phosphatase label, in which the results of a reaction catalyzed by alkaline phosphatase is observed, and may be used to identify an analyte or verify its presence in a sample, and may be used to quantify an analyte in a sample. Alkaline phosphatase reagents are commercially available; for example, Nitroblue Tetrazolium (NBT) is used with the alkaline phosphatase substrate 5-Bromo-4-Chloro-3-Indolyl Phosphate (BCIP) to provide a colored product which may be observed and quantitated. Other reagents include Fast Red TR/Naphthol AS-MX and TR phosphate (4-Chloro-2-methylbenzenediazonium/3-Hydroxy-2-naphthoic acid 2,4-dimethylanilide phosphate, reagents for the production of p-nitrophenol, and others.

For example, a label may be a peroxidase label (such as horseradish peroxidase, myeloperoxidase, or other peroxidase) in which the results of a reaction catalyzed by the peroxidase is observed, and may be used to identify an analyte or verify its presence in a sample, and may be used to quantify an analyte in a sample. Benzidine-containing compounds (e.g., diaminobenzidine, tetramethyl benzidine), aniline-containing compounds, aminoantipyrene compounds, Trinder reagents, and other reagents known in the art may be used to provide a detectable product in the presence of a peroxidase.

A label may be a dye, such as rhodamine and related rhodamine dyes (e.g., tetramethylrhodamine (TMR), carboxytatramethyl rhodamine (TAMRA), and others), fluorescein and fluorescein derivatives (e.g., 5-carboxyfluorescein, 6-carboxy fluorescein and others), phycoerythrin, umbelliferone, Texas Red, rare earth chelates (europium chelates), dansyl dyes (including, e.g., dansylamide dyes, dansyl cadaverine, dansyl chloride, and others); cyanine dyes (e.g., Cy3, Cy5, SYBR green, and others); Lissamine; phycoerythrins; Texas Red; and analogs thereof.

A label may be a fluorescent material, including fluorescent dyes, and including green fluorescent protein and other fluorescent proteins known in the art. A label may be a luminescent moiety, such as luminol, or other luminescent material, including bioluminescent materials such as luciferase, luciferin, and aequorin.

A label may be a nanoparticle, such as a gold nanoparticle (e.g., a colloidal gold particle), or a quantum dot (e.g., a small particle, typically a semiconductor, which may be detectable upon application of an appropriate amount and wavelength of electromagnetic radiation, e.g., by illumination). A label may be a magnetic label, or a paramagnetic label, which may be a nanoparticle or bead. A label may be a radioisotope or other radioactive material, including, e.g., $^{131}$I, $^{125}$I, $^{111}$In, $^{199}$Tc, $^{35}$S, $^{14}$C, and $^{3}$H.

As used herein, a "capture element" is used to link a molecule to another molecule or to a support, such as a solid support. A capture element may be, for example, a polynucleotide, a polypeptide, a peptide nucleic acid, a locked nucleic acid, an oligosaccharide, a polysaccharide, an antibody, an antibody fragment, an antibody mimic, an immunoadhesin, a receptor, a ligand, a lipid, biotin, avidin, streptavidin, Extravidin, neutravidin, or other avidin derivative or avidin analog, a metal, an epitope tag, and any portion of any of these. A capture element binds to a binding partner, such as a tag; e.g., where the capture element is an antibody or antibody fragment, the tag is the corresponding antigen to which the antibody or antibody fragment specifically binds. For example, a capture element may include a biotin group or a biotin binding protein such as, e.g., avidin, streptavidin, neutravidin, or Extravidin. In further examples, a capture element may be either polyhistidine or nitrilotriacetic acid (NTA) chelated with a metal ion such as nickel, cobalt, iron, or any other metal ion able to form a coordination compound with poly-histidine when chelated with NTA. A capture element may be or include a polynucleotide that is designed to hybridize directly with a complementary nucleic acid sequence.

As used herein, a "capture surface" is a solid surface, which may be free floating (e.g., a bead) or may be attached to, or part of, a structure (e.g., a wall of a tube, or a side of a dish or flask). A capture surface may include capture elements effective to link a labeled compound to the capture surface. For example, a capture surface may comprise avidin where a labeled compound comprises biotin; may comprise an antibody (e.g., an anti-sheep antibody, where the antibody that binds the target analyte is a sheep antibody); a combination of these; and may comprise any other agent, or any combination of these or other agents, effective to link a compound to a capture surface.

As used herein, a "low pH" refers to a pH of between about pH 2 to about pH 6, or, in some instances, a pH range of between about pH 2.5 to about pH 5.5, or more particularly, a pH range of between about pH 3 to about pH 5, or between about pH 2.5 to about pH 4.

As used herein, a "neutral pH" refers to a pH of between about pH 6 to about pH 9, or, in some instances, a pH range of between about pH 6.5 to about pH 8.5, or more particularly, to a pH range of between about pH 7 to about pH 8.

As used herein, the term "aspartyl peptidase" refers to a protelytic enzyme with an active site containing an aspartate residue. Aspartyl peptidases are classified within Enzyme Commission (EC) number EC 3.4.23 (e.g., pepsin A (EC 3.4.23.1), pepsin B (EX 3.4.23.2), pepsin C or gastricsin (EC 3.4.23.3) and chymosin (EC 3.4.23.4)). Aspartyl peptidases include digestive, lysozomal, bacterial, fungal, viral and other proteases. Aspartyl peptidases typically are most active under acidic conditions, such as, for example, a pH range of between about pH 2 to about pH 6, or, in some instances, a pH range of between about pH 3 to about pH 5,or other acidic pH range. Aspartyl peptidases include, without limitation, for example, pepsin (including pepsin A, B, and C), gastricsin, chymosin (rennin), cathepsin, renin, HIV protease, plasmepsin, retropepsin, and nepenthesin. A more particular, but not exhaustive, list of aspartyl peptidases includes pepsin A (*Homo sapiens*), cathepsin D (*Homo sapiens*), nepenthesin (Nepenthes gracilis), walleye dermal sarcoma virus retropepsin (walleye dermal sarcoma virus), Ty3 transposon peptidase (*Saccharomyces cerevisiae*), Gypsy transposon peptidase (*Drosophila melanogaster*), Osvaldo retrotransposon peptidase (*Drosophila buzzatii*), retrotransposon peptidase (*Schizosaccharomyces pombe*), retrotransposon 17.6 peptidase (*Drosophila melanogaster*), cauliflower mosaic virus-type peptidase (cauliflower mosaic virus), bacilliform virus peptidase (rice tungro bacilliform virus), thermopsin (*Sulfolobus acidocaldarius*), signal peptidase II (*Escherichia coli*), spumapepsin (human spumaretrovirus), Copia transposon peptidase (*Drosophila melanogaster*), Ty1 transposon peptidase (*Saccharomyces cerevisiae*), presenilin 1 (*Homo sapiens*), impas 1 peptidase (*Homo sapiens*), and yeast proteinase A.

As used herein, the term "aspartyl peptidase active at low pH" refers to an aspartyl peptidase that is active within a pH range of between about pH 2 to about pH 6, or, in some instances, a pH range of between about pH 3 to about pH 5, or between about pH 2.5 to about pH 4. An aspartyl peptidase active at low pH is inactivated (i.e., its activity is reduced significantly reduced) at neutral and basic pH. For example, the peptidase activity of an aspartyl peptidase active at low pH is reduced by greater than about 50%, or by greater than about 75%, at pH 8.

As used herein, an enzyme (e.g., such as a peptidase) is "active" or "activated" when, in the presence of sufficient substrate, the rate or extent of a reaction catalyzed by the enzyme is at or near normal levels, and an enzyme (e.g., such as a peptidase) is "inactive" or "inactivated" when, in the presence of sufficient substrate, the rate or extent of a reaction catalyzed by the enzyme is reduced significantly below normal levels, or is negligible or absent.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. Typically, only a small amount of blood is collected in this way (e.g., the amount of blood may be about 250 μL or less, or about 200 μL or less, or about 150 μL or less, or about 100 μL or less, or about 50 μL or less, or about 25 μL or less, or about 15 μL or less, or about 10 μL or less, or about 10 μL or less, or about 5 μL or less, or about 3 μL or less, or about 1 μL or less). Blood from a finger-stick may be collected, e.g., by needle, syringe, capillary tube, or other method. Blood from a finger-stick may be collected for transport to another location; for storage prior to use or analysis; for immediate use; or for a combination of the same.

Assay methods disclosed herein provide fast assays, in part because denaturation in acid is fast and allows the aspartyl peptidase (e.g., pepsin) to digest vitamin D binding protein rapidly. In addition, although vitamin D binding protein has a high affinity for vitamin D and so could compete with an antibody for vitamin D, degradation of the binding protein by the aspartyl peptidase rapidly destroys the ability of the binding protein to bind vitamin D, and so soon reduces and eliminates such competition, providing a rapid and accurate assay of vitamin D levels.

Measurement of free vitamin D may be made using molecules which specifically bind to vitamin D or to a particular species of vitamin D (for example, anti-vitamin D antibodies such as anti-25-hydroxy vitamin D antibodies). As noted previously, the major forms of vitamin D circulating in blood are 25-hydroxy vitamin D3 and 25-hydroxy vitamin D2. Since levels of different forms of vitamin D are clinically relevant (e.g., D2 and D3 forms of vitamin D), different binders may be used in detecting vitamin D and in measuring vitamin D levels. Thus, for example, in embodiments, a binding molecule for 25-hydroxy vitamin D3 and a binding molecule for 25-hydroxy vitamin D2 may be used, alone or together, in assays and methods as disclosed herein. In embodiments, molecules which bind more than one form of vitamin D may be used. For example, a binding molecule for 25-hydroxy vitamin D3 and a binding molecule for 25-hydroxy vitamin D2 may be used, alone or together, in assays and methods as disclosed herein. A binding molecule that binds both 25-hydroxy vitamin D2 and 25-hydroxy vitamin D3 may be used. Mixtures of these, and other such binders, may be used in assays as disclosed herein. In embodiments, other binders, including other antibodies, e.g., antibodies to non-hydroxylated vitamin D, to di-hydroxylated vitamin D, etc., may be used.

In embodiments, assays are provided in which binders (e.g., antibodies) specific for vitamin D are used to determine the amounts of vitamin D in a sample. For example, in embodiments, assays are provided in which binders (e.g., antibodies) specific for a 25-hydroxy form or forms of vitamin D are used to determine the amounts of vitamin D in a sample. In embodiments where a binder specific for one particular form of vitamin D is used, assays specific for that form of vitamin D are provided. For example, where a binder specific for 25-hydroxy vitamin D3 is used, the methods disclosed herein may be used to quantify vitamin D3 in a sample. Multiple binders may be used together; e.g., a binder specific for 25-hydroxy vitamin D2 and a binder specific for 25-hydroxy vitamin D3 may be used together to quantify 25-hydroxy vitamin D2 and 25-hydroxy vitamin D3 forms of vitamin D. For example, assays disclosed herein may use antibodies which bind both 25-hydroxy vitamin D2 and 25-hydroxy vitamin D3, albeit with unequal affinities, in amounts so as to provide substantially the same detection for both 25-hydroxy vitamin D2 and 25-hydroxy vitamin D3.

In embodiments, assays may use VDBP as the binder to measure levels of 25-hydroxy vitamin D2 and 25-hydroxy vitamin D3, or other forms of vitamin D. In addition, embodiments of the methods and assays disclosed herein include any other assay where an analyte is bound to an endogenous binding protein or set of binding proteins or other "binder" where the analyte is released and may be quantified following denaturation and enzymatic degradation of the binding protein by use of an aspartyl peptidase under acidic conditions.

Embodiments of the methods and assays disclosed herein include embodiments utilizing any proteolytic enzyme that is active under conditions likely to denature the vitamin D binding protein, where the proteolytic enzyme can be inactivated (e.g., becomes inactive at neutral pH, upon dilution, or heating, or other condition).

In embodiments of the methods and assays disclosed herein, reagents may be provided in liquid form. In embodiments, liquid reagents may be provided in pre-filled, sealed containers ready for use in an assay when needed. In embodiments, liquid reagents provided in pre-filled, sealed containers may be sterile reagents, and the pre-filled, sealed containers may be sterile containers.

In embodiments of the methods and assays disclosed herein, reagents may be provided in dry form (e.g., may be lyophilized, or provided as a powder, or as a cake, or other solid form). In embodiments, dry reagents may be provided in pre-filled, sealed containers ready for use in an assay when needed. In embodiments, dry reagents provided in pre-filled, sealed containers may be sterile reagents, and the pre-filled, sealed containers may be sterile containers. In embodiments, containers with dry reagents may be configured for introduction of liquid effective to dissolve a dry (e.g., a lyophilate, a powder, a cake, or other solid) reagent.

In embodiments of the methods and assays disclosed herein, a capture surface may be preformed and dried. Such a capture surface may be prepared, for example, using methods disclosed in U.S. Pat. No. 8,088,593. In addition, pepsin may be dried (lyophilized) into a container, such as a tube, caplet, vial, cuvette, or other container; the container may subsequently be sealed. Dried pepsin may be dissolved in an appropriate solution or solvent, such as, e.g., 100 mM citrate buffer (about pH 2 to 3, e.g., pH 2.6) prior to use in an assay. Other reagents used in assays as disclosed herein may also be sealed into containers (such as tubes) and packed together into a kit for use in an assay as disclosed herein. Such a kit may be sealed, labeled and bar-coded prior to shipping to customers and other users.

In embodiments, a blood sample may be obtained from a subject by performing a finger-stick, and collecting blood liberated thereby from the subject. Typically, only a drop or only a small amount of blood is collected in this way. Blood from a finger-stick may be collected, e.g., by needle, syringe, capillary tube, or other method. For example, when collected by capillary tube, an outer end of the glass capillary may be touched to the blood droplet so that blood is drawn by capillary action into the capillary tube for use in analysis by flow to a collection or analysis device, or by transfer of the tube itself, or for analysis within the tube.

EXAMPLES

The following examples provide descriptions of embodiments of the methods disclosed herein. These methods of measuring vitamin D were applied to clinical blood samples, including plasma, serum, and whole blood, as discussed below. The following list and description of materials describes some of the materials used in performing the assays and measurements described in the following exemplary methods.

"TRIS®-buffered saline" (TBS) was (Tris(hydroxymethyl)aminomethane in saline, supplied as 10× solution; when diluted, TBS contained about 20 mM TRIS® and 0.9% NaCl, at about pH 7.4. TBS was obtained from Sigma.

"Low BSA 0.03% in TB S" was 0.03% bovine serum albumin (BSA) and "3% BSA in TBS" was 3% BSA (Fraction V, 99% Pure) in 50 mM TBS, with 0.05% Sodium Azide, pH 8.0 (Sigma Catalog #3059).

"Wash buffer" was 50 mM TBS, 0.05% Tween 20, 0.05% Sodium azide, pH 8.

Other buffers (e.g., carbonate-bicarbonate buffer) and reagents (e.g., citric acid and sodium citrate) were also obtained from Sigma. For example, citric acid (anhydrous) is Sigma catalog #251275, and sodium citrate (dihydrate) is Sigma catalog # S1804.

Citrate buffer was made as follows: 900 mL of HPLC grade water was added to 17.77 g Citric Acid (anhydrous) and 4.27 g Sodium Citrate (dihydrate), and the solution was mixed until the solids were dissolved; the pH was checked with a calibrated pH meter. If the measured pH was not within the range of pH 2.4 to pH 3.0, the solution was discarded. The pH was adjusted (when necessary) to 2.6 using 1N NaOH or HCl, while on a mixing stand. If pH adjustment led to overshooting of the pH, the buffer was discarded. Upon adjustment to pH 2.6, water was added to provide a final volume of 1 L buffer.

The following buffers were obtained from Pierce: "Super Block", a TRIS®-buffered saline, pH 7.4, with Kathon preservative and containing a proprietary protein formulation (Pierce Catalog #37535); "Starting Block", a TBS (Pierce Catalog #37542); "Sea Block", a PBS (Pierce Catalog #37527); and "Protein Free", a TBS lacking protein (Pierce Catalog #37570).

25-hydroxy vitamin D3 and 25-hydroxy vitamin D2 were obtained from Sigma (Sigma-Aldrich Corporation, Saint Louis, Mo.). Vitamin D conjugates were obtained from Dojindo (Dojindo Molecular Technologies, Rockville, Md.).

Anti-vitamin D antibodies were obtained from commercial suppliers. A monoclonal antibody directed to 25-hydroxy vitamin D3 (catalog no. ABIN108769) was obtained from Antibodies-Online (Atlanta, Ga., USA). A monoclonal antibody directed to 25-hydroxy vitamin D3 (catalog no. MAB6566) was obtained from R&D Systems (Techne Corp., Minneapolis, Minn., USA). Sheep anti-vitamin D antibodies were obtained from Bioventix (Sheep Monoclonal Anti 25-Hydroxyvitamin D Antibodies, Bioventix catalog no. BVX.vitD3.5H10 ("Ab5H10"); catalog no. BVX.vitD2.2D10 ("Ab2D10"); and catalog no. BVX.vitD3.2F4 ("Ab2F4"); Bioventix Inc., Farnham, Surrey, U.K.). Other antibodies were obtained from Fitzgerald (biotin-conjugated rabbit anti-Sheep IgG (Fc), catalog no. 43C-CB1326, a rabbit polyclonal antibody that binds to epitopes on the Fc portion of sheep IgG antibodies); Fitzgerald Industries International, Inc., Acton, Mass.).

Pepsin was porcine gastric mucosa pepsin (Sigma catalog # P7000) unless otherwise stated.

Example 1: Total 25-Hydroxy Vitamin D Assay

A biotin-labeled anti-sheep antibody coated on UltraAvidin™ served as the capture surface. Tests were performed with a final antibody concentration of 50 ng/mL and biotin conjugate of 1:10,000 from stock. Super Block (Pierce Catalog #37535) produced the best modulation.

Alkaline Phosphatase Conjugate

A custom 25-hydroxy vitamin D3 alkaline phosphatase (AP) conjugate was tested in the assay system with the following format: biotin-labeled anti-sheep antibody surface, with the unlabeled analyte competing with the AP labeled analyte unlabeled sheep anti-25-hydroxy vitamin D antibody in solution. This format and conjugate was used for initial assay screening and a final sample dilution of 1:5 was used to allow comparison between methods as disclosed herein using the custom conjugate and the commercial 25-hydroxy vitamin D biotin conjugate. The custom 25-hydroxy vitamin D-AP conjugate with the anti-sheep surface was validated for use in the present assay methods. StabilZyme® AP Conjugate Stabilizer (SurModics, Eden Prairie, Minn. 55344, USA, Stock Code SA01-0050) was chosen as a suitable alkaline phosphatase stabilizing diluent.

Pretreatment of Serum or Plasma Samples

Pepsin was lyophilized in a reagent tube and reconstituted (dissolved) with citrate buffer during the assay procedure. (Pepsin from porcine gastric mucosa and from other sources yielded similar results.) The pepsin was lyophilized at 480 µg per reaction tube, the automated protocol moved 48 µL of citrate buffer into the tube, which was then dissolved and mixed prior to use. The results obtained using reconstituted, previously lyophilized pepsin and liquid pepsin were substantially equivalent.

Serum and plasma samples were diluted 1:5 into a solution of 10 mg/mL pepsin (in 100 mM citrate buffer at pH 2.6) and incubated for 5 minutes at 34° C. To stop the pepsin digestion and inactivate the pepsin, the reaction mixture was further diluted 1:10 into 50 mM TRIS pH 8.0 (final sample dilution 1:50). The resulting pretreated diluted sample solution can be used immediately in an immunoassay for vitamin D.

Pepsin Sample Treatments and Assay of Vitamin-D

In this example, anti-25-hydroxy vitamin D antibodies were used to detect vitamin D. Antibodies to other forms, or to multiple forms, of vitamin D may also be used. Binders other than antibodies may be used.

Pepsin was used to free vitamin D from VDBP for quantitative measurements of vitamin D in blood samples. Use of pepsin has not been reported for vitamin D (e.g., 25-hydroxy vitamin D) assays. Binding of 25-hydroxy vitamin D to VDBP would be expected to decrease at acidic pH, a pH range in which pepsin is active and will digest VDBP. Thus, the combination of very low pH and the digestion by pepsin work synergistically to enhance the release of 25-hydroxy vitamin D and thus to improve the speed and accuracy of vitamin D measurements.

However, low pH alone did not provide optimal conditions for the assays and methods disclosed herein. Use of strong acid alone, such as HCl, was found to cause precipitation and clumping of the sample plus reagent solutions, making vitamin D measurements difficult. In addition, use of strong acid alone, such as HCl, did not provide stable or repeatable final pH values following sample addition. It was surprisingly found that low pH buffered solutions, such as citrate buffered solutions (e.g., citrate buffers of about pH 2.4 to about pH 3.0, preferably pH 2.6) provided favorable conditions for aspartyl peptidase denaturation and degradation of VDBP for the release of vitamin D, while providing stable and repeatable pH values following sample addition. Accordingly, Applicants disclose herein aspartyl peptidase-based methods for assaying vitamin D levels in blood samples that utilize low pH buffered solutions, including low pH citrate buffers.

Samples were pre-treated as described above. The assay system and general method used are as described above, and may use devices, systems, and methods as described in U.S. Pat. No. 8,088,593; in U.S. Pat. No. 8,380,541; in PCT/US012/57155, filed Sep. 24, 2012; and in U.S. patent application Ser. No. 13/244,947, filed Sep. 26, 2011. Reagents were: Pepsin: the pepsin solution was 10 mg/mL porcine pepsin in 100 mM citrate buffer pH 2.6 (final pH 3.9 following addition of pepsin). (The pepsin used was from porcine gastric mucosa; other experiments confirmed that similar results were obtained with pepsin from other sources.) Unless otherwise stated, the pepsin was lyophilized at 480 µg per reaction tube, the automated protocol moved 48 µL of citrate buffer into the tube, which was then dissolved and mixed prior to use. Labeled Conjugate: Alkaline phosphatase (calf intestine)-labeled 25-hydroxy-vitamin-D3 (concentration estimated at about 10 ng/mL with a hapten/enzyme ratio of 4:1). The chemiluminogenic alkaline phosphatase substrate was Phospho-Glo Substrate (KPL). Wash: The Wash buffer was 50 mM TBS, 0.05% Tween 20, 0.05% Sodium azide, pH 8. Substrate: Polystyrene reaction vessels, coated with UltraAvidin™ as described in U.S. Pat. No. 8,088,593, were used for these assays. (During manufacturing: UltraAvidin™-coated tips were exposed first to biotinylated rabbit antibody then washed and "blocked" with a commercially available blocking buffer.)

The liquid phase of the assay reaction included the sample (mixed with the sample diluent) and included the anti-vitamin-D antibodies and the alkaline phosphatase (AP) conjugate. As discussed below, in many cases mixtures of two types of anti-vitamin D antibodies were used. For example, in many cases, the anti-vitamin-D antibodies Ab5H10 and Ab2F4 were mixed into the diluted sample (final concentrations 10 ng/mL Ab5H10 and 5 ng/mL Ab2F4), and then the AP conjugate was mixed into the solution that included the sample, the sample diluent, and the anti-vitamin-D antibodies. This liquid mixture was incubated with the capture surface (anti-sheep antibody bound to UltraAvidin™-coated polystyrene).

After extensive optimization of buffer, pH, concentration and dilutions using manual sample treatments, assay conditions which provided good sensitivity and low variance vitamin D measurements were identified. In initial experiments, blood samples were manually diluted 1:5 into a solution of 10 mg/mL pepsin in 100 mM citrate buffer pH 2.6, incubated for 5 minutes at 37° C. and then further diluted 1:10 into 50 mM TRIS pH 8.0 to neutralize the sample and permanently inactivate the pepsin (providing a final sample dilution of 1:50). Vitamin D controls were obtained from Immunodiagnostic Systems, Inc. ("IDS", Scottsdale, Ariz. USA 85258). The dose response results obtained for the IDS serum-based vitamin D calibrators and for the clinical samples were in good agreement.

Vitamin D assay methods using pepsin degradation of vitamin D binding proteins at low pH were then further optimized in subsequent experiments, including experiments performed at an operating temperature of 34° C. It was determined that a pepsin pre-incubation step was not required, as it was found that the requisite digestion of carrier proteins took place within the time (approximately 3 minutes) taken to mix the sample into the extraction buffer. Thus, further assay conditions using pepsin were determined which did not require extensive pre-incubation of the sample. This sample treatment and assay protocol consisted of a 1:5 dilution of the sample into 10 mg/mL pepsin in 100 mM citrate buffer pH 2.6, followed by a 1:8 dilution into 50 mM TRIS pH 8.0 which brought the pH of the diluted sample to 8.0 and neutralized the pepsin. Then the sheep anti-25-hydroxy vitamin D antibody was added and incubated with the sample for 10 minutes. Following addition of the anti-25-hydroxy vitamin D antibody, the 25-hydroxy vitamin D-AP conjugate was added, resulting in a final sample dilution of 1:50. The mixture was then incubated on the anti-sheep capture surface for 5 minutes, followed by a wash and 5 minute substrate incubation.

The assay protocol steps were performed by automated device. The following assay protocol was used:

1. Sample was diluted 1:5 into 100 mM Citrate buffer pH 2.6 containing 10 mg/mL pepsin and mixed (final pH 3.9) for 5 minutes at 34° C.
2. Treated sample was diluted a further 1:8 into 50 mM TRIS buffer pH 8.0 to permanently deactivate the pepsin, and anti-25-hydroxy vitamin D antibody in a blocking buffer was spiked in and mixed. This mixture was incubated for 10 minutes.
3. The AP-labeled 25-hydroxy vitamin D was added to the sample mixture and then transferred to the capture surface (biotinylated anti-sheep secondary antibody bound to UltraAvidin™-coated polystyrene) and incubated for 5 minutes.
4. The surface was washed six times (1 minute for each wash cycle) with 0.05% Tween20® in 50 mM TBS containing 0.05% sodium azide at pH8.0.
5. The washed capture surface was exposed to enzyme substrate for five minutes and the chemiluminescence was read in an automated luminometer.

Figure 4:
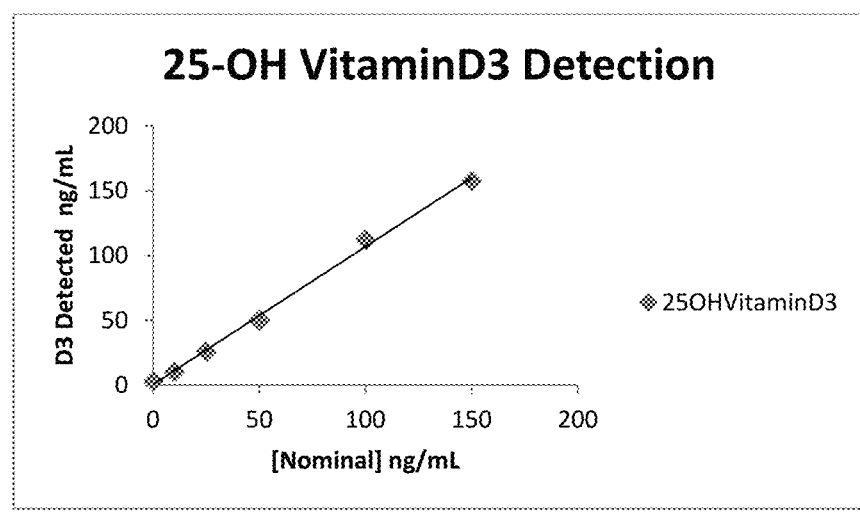
FIG. 4 shows vitamin D measurements using an anti-25-hydroxyvitamin D antibody, showing measured values of 25-hydroxyvitamin D3 (vertical axis) plotted against the nominal amounts of 25-hydroxyvitamin D3 spiked into the low BSA buffer.

Assays using anti-25-hydroxyvitamin D antibodies were able to determine the amount of vitamin D (e.g., as 25-hydroxyvitamin D, in both the D2 and D3 forms). The antibodies used had high affinity for the 25-hydroxy vitamin D3-Alkaline Phosphate conjugate used in the assay. As shown in the example shown in FIG. 4, sheep monoclonal antibody Ab2F4 was able to detect 25-hydroxyvitamin D3 following pepsin treatment to release vitamin D from VDBPs.

Figure 5:
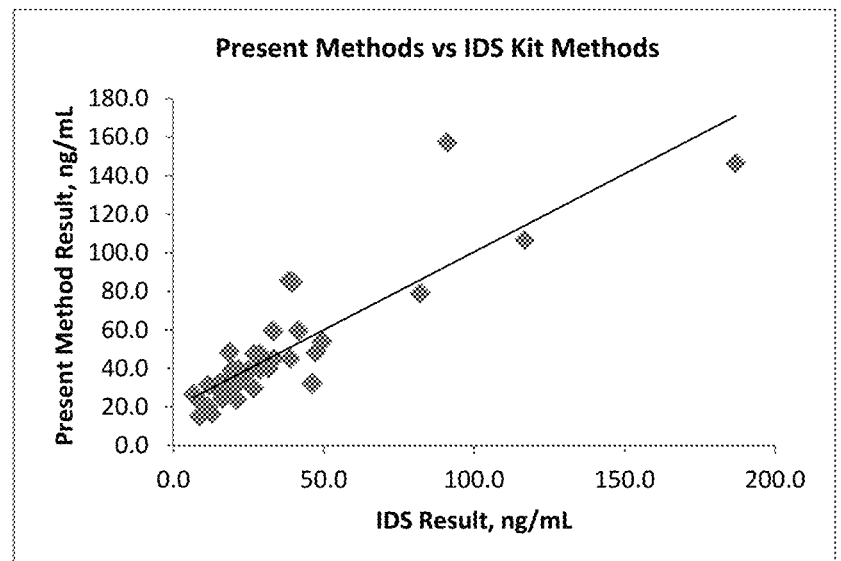
FIG. 5 shows clinical correlation between the results of the present method using pepsin treatment and an anti-vitamin D antibody, compared with the results obtained by use of an IDS EIA Kit.

FIG. 5 presents results of vitamin D measurements on clinical (serum) samples obtained according to the methods of Example 1, using a sheep anti-25-hydroxy vitamin D antibody (AB5H10), shown compared to results obtained with a commercially available method. The commercially available method used in this example was the IDS EIA Kit ° test (Immuno Diagnostic Systems Ltd., Scottsdale, Ariz., USA), enzyme immunoassay. The results were quite similar with both methods, confirming the usefulness of the methods disclosed herein.

The Regression equation shown in FIG. 5 has the following parameters:

$y=0.81\times(\text{IDS result, ng/mL})+19.43$; $R=0.869$; $R^2=0.7564$ where "×" indicates multiplication.

Example 2: Balancing 25-Hydroxy Vitamin D3 and 25-Hydroxy Vitamin D2 Reactivity

Figure 6A:
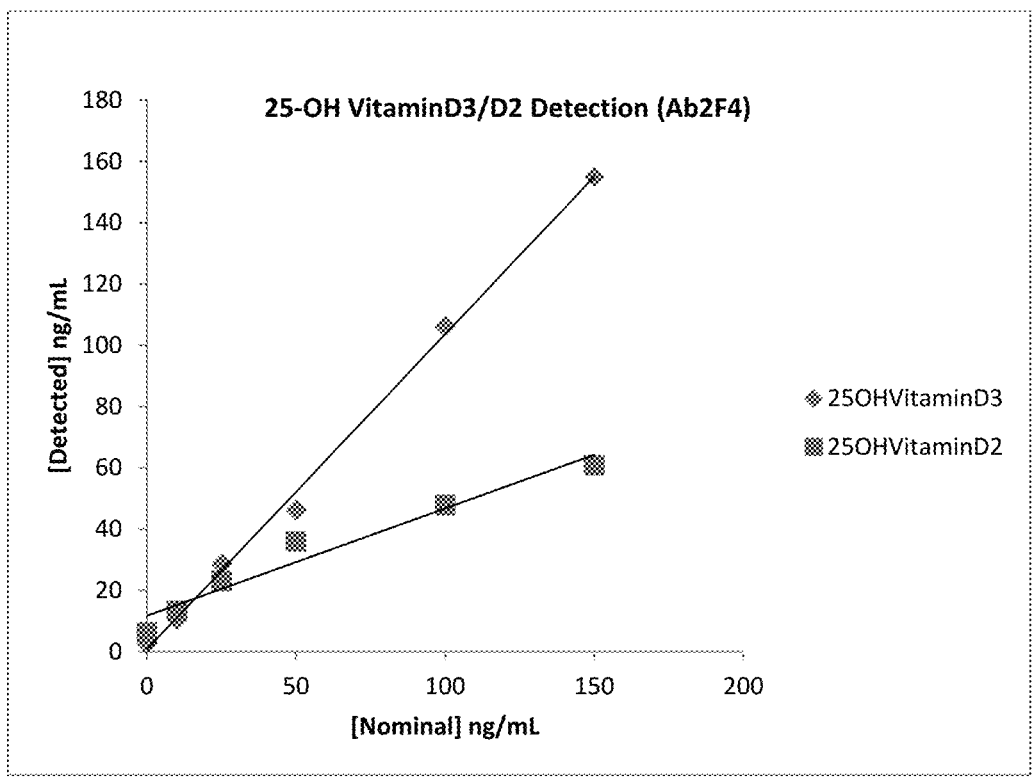
FIG. 6A shows vitamin D measurements using an anti-25-hydroxyvitamin D antibody (Ab2F4), showing measured values of 25-hydroxyvitamin D2 and 25-hydroxyvitamin D3 (vertical axis) plotted against the nominal amounts of 25-hydroxyvitamin D2 and 25-hydroxyvitamin D3 spiked into the low BSA buffer.

Assays using anti-25-hydroxyvitamin D antibodies were able to determine the amount of vitamin D (as 25-hydroxy vitamin D, in both the D2 and D3 forms). As shown in the example shown in FIG. 6A, sheep monoclonal antibody Ab2F4 was able to detect both 25-hydroxy vitamin D2 and 25-hydroxy vitamin D3. Screening of several sheep monoclonal antibodies reactive for both forms of 25-hydroxy vitamin D showed that Ab5H10 produced the best dose response, but had higher affinity for 25-hydroxy vitamin D2 than for 25-hydroxy vitamin D3, whereas Ab2F4 had higher reactivity for 25-hydroxy vitamin D3 than 25-hydroxy vitamin D2. Both antibodies had high affinity for the 25-hydroxy vitamin D3-Alkaline Phosphate conjugate used in the assay.

Figure 6B:
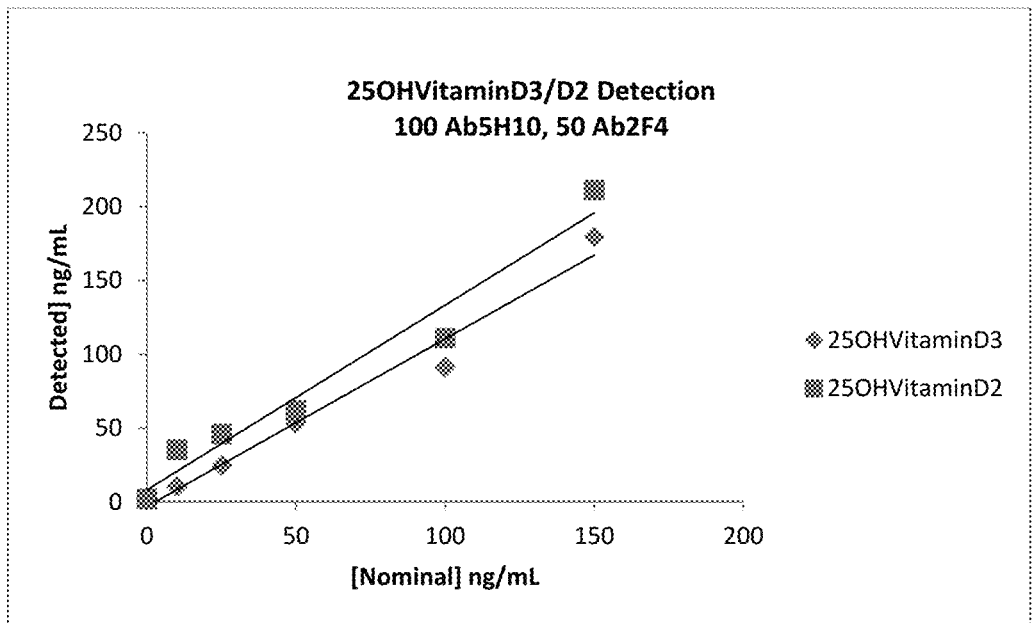
FIG. 6B shows vitamin D measurements using a mixture of two anti-25-hydroxyvitamin D antibodies (Ab5H10 and Ab2F4, in a ratio of 2:1 by weight/mL, respectively), showing measured values of 25-hydroxyvitamin D2 and 25-hydroxyvitamin D3 (vertical axis) plotted against the nominal amounts of 25-hydroxyvitamin D2 and 25-hydroxyvitamin D3 spiked into the low BSA buffer.

In order to achieve a more balanced reactivity for the forms, the antibodies were combined in different proportions. This experiment was performed with Sigma analytes diluted in low BSA buffer (0.03% BSA in TBS). It was determined that a 2:1 ratio of Ab5H10 to Ab2F4 produced the best results; a mixture of 100 ng/mL Ab5H10 and 50 ng/mL Ab2F4 produced the best balance of reactivity to 25-hydroxy vitamin D3 and 25-hydroxy vitamin D2, with 100% reactivity to both forms in the clinical range. As shown in FIG. 6B, the 2:1 mixture of two sheep antibodies was able to detect both 25-hydroxy vitamin D2 and 25-hydroxy vitamin D3, with a combined affinity that was substantially the same for both the D2 and D3 forms.

A set of 45 clinical samples was run to confirm the performance of the final assay protocol. A calibration curve was created in Low BSA buffer (0.03% BSA in TBS). As discussed above, better results were obtained using balanced mixtures of anti-vitamin D antibodies than were obtained using one anti-25-hydroxy vitamin D antibody alone; the balance of reactivity to 25-hydroxy vitamin D3 and 25-hydroxy vitamin D2 was optimized using 2:1 ratios of anti-vitamin D antibodies Ab5H10 and Ab2F4.

The dose-response curve for such assays was determined which provides a fit to the original data from clinical samples. The dose-response curve of an exemplary experiment was fitted with the following equation:

$$Conc=28.313\times(((18944.016-1897.831)/(RLU-1897.831))-1)^{\wedge}(1/2.597)$$

Where "x" indicates multiplication, and ^ indicates exponentiation.

Example 3: Correlation of Assay Results with Those of Prior Methods

Figure 7:
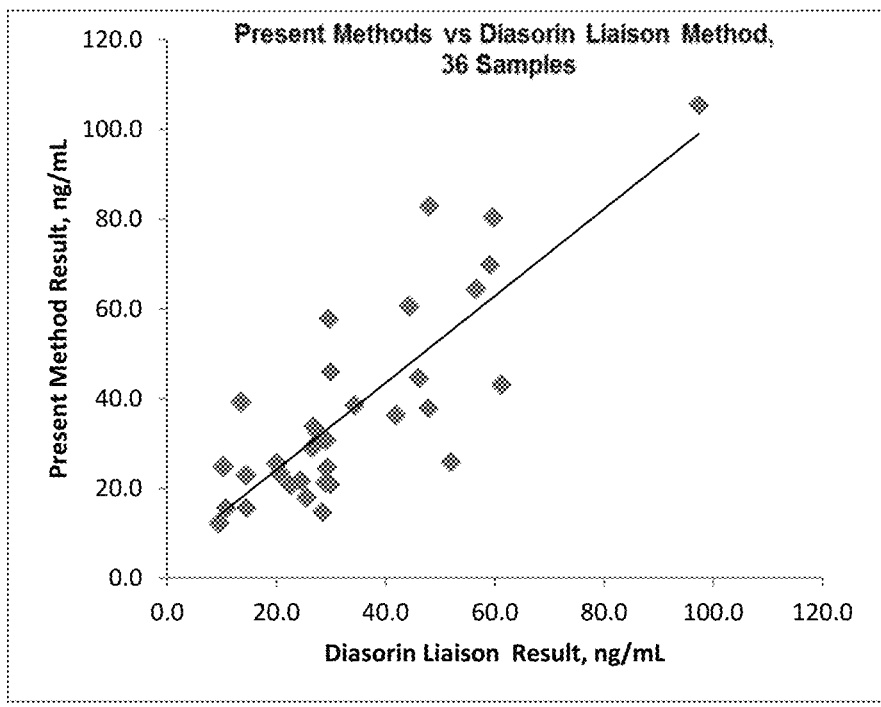
FIG. 7 shows correlation between vitamin D measurements according to the methods of Example 3 (using two anti-vitamin D antibodies) as compared to the results of standard methods for clinical (serum) samples.

Clinical samples were obtained which had a range of 25-hydroxy vitamin D concentrations; these samples were tested with the IDS kit, with the Diasorin Liaison® methods, and with the present methods as disclosed herein. FIG. 6 presents results of 25-hydroxy vitamin D measurements on clinical (serum) samples obtained according to the methods of Example 1, where the anti-25-hydroxy vitamin D antibody used in these measurements was a 2:1 mixture of Ab5H10 and Ab2F4 (final concentrations, 10 ng/mL Ab5H10 and 5 ng/mL Ab2F4). These results are shown compared to results obtained with the Diasorin Liaison® method, a test that is widely used in the art. The Diasorin Liaison® test (DiaSorin Corporation, Stillwater, Minn.) is a chemiluminescent assay in which serum was incubated with antivitamin-D coated microparticles and isoluminol derivative-conjugated 25-hydroxy vitamin D before measurement of the chemiluminescent signal. Correlation of the present methods with the Diasorin Liasion® assay results were very good. A graph showing the results from the Diasorin Liaison® assay and the results obtained by the methods disclosed herein is presented in FIG. 7. The Regression equation shown in FIG. 7 has the following parameters:

$$y=0.97\times(Diasorin\ Liaison\circledR,\ ng/mL)+4.8;\ R=0.81;$$
$$R^2=0.664$$

where "x" indicates multiplication.

The results of the present methods applied to these samples was also compared to results on these samples using the IDS EIA Kit® test, an enzyme immunoassay available from Immuno Diagnostic Systems Ltd., Scottsdale, Ariz., USA. Correlation of the present methods with the IDS EIA kit results were also very good. However, with respect to the IDS EIA results, one sample point was considered an outlier, as the results for this point obtained using the IDS kit appeared to be clearly different from the results obtained by the Diasorin method and from the results obtained by the present methods. This difference was possibly due to the presence of high levels of 25-hydroxy Vitamin D2 in this sample and to the fact that the IDS EIA kit reports only 75% of the D2 form of vitamin D (see, e.g., Hollis, Clinical Chemistry 46(10):1657-1661 (2000) and Carter et al., Clinical Chemistry 50(11):2195-2197 (2004)), whereas the present methods and Diasorin systems fully report the vitamin D2 content of samples. Thus, with the possible exception of the one point mentioned above, the results were quite similar with all methods, and the results of the present methods correlate well with those of other tests used in the art. These results confirm that the methods disclosed herein are suitable for the measurement of vitamin D.

Example 4: Cross Reactivity

Tests were performed in order to determine whether non-target compounds could interfere with the assay results. Such tests, termed "cross-reactivity tests", measured the change in measured 25-hydroxy vitamin D due to the presence of a non-target substance by comparing the value of 25-hydroxy vitamin D measured by the present methods where a potentially interfering compound was in the sample, as compared to the value of 25-hydroxy vitamin D measured by the present methods in the absence of the potentially interfering compound. Cross reactivity testing was conducted using the final assay conditions in a low BSA buffer matrix (0.03% BSA in TBS). Cross-reactivity was reported in these assays as % recovery=100×([measured vitamin D])/([nominal vitamin D]); [measured vitamin D] is the 25-hydroxy vitamin D concentration measured in the presence of the potentially interfering compound, and [nominal vitamin D] is the 25-hydroxy vitamin D concentration measured in the absence of the potentially interfering compound. In general, a % recovery value between about 85% and about 115% does not indicate significant cross-reactivity, while a % recovery value greater than about 115% indicates cross-reactivity. (Note that an interfering compound would displace labeled 25-hydroxy vitamin D in the competition assays disclosed herein, so that the interfering compound would cause an apparent (erroneous) increase in the measured 25-hydroxy vitamin D.) For comparison, values for 25-hydroxy vitamin D3 (a direct target of the assay, and not a cross-reactant) are presented in the table.

No cross reactivity was observed with vitamin D3 (Cholecalciferol), vitamin D2 (Ergocalciferol), or 24,25-dihydroxy vitamin D3 as the potentially interfering compounds. Some cross reactivity was observed with 1α,25-dihydroxy vitamin D3 (another hydroxylated metabolite of vitamin D) as the potentially interfering compound. Such cross-reactivity does not present any clinical concerns because blood levels of 1α,25-dihydroxy vitamin D are in the pg/mL range, and so are on the order of 1000-fold lower than 25-hydroxy vitamin D, so that any possible effects would be negligible. Cross reactivity with this metabolite is common in 25-Hydroxyvitamin D assays.

Reported cross reactivity for various other 25-hydroxy vitamin D methods are reported below for comparison. Table 1 reports cross-reactivity for various forms of vitamin D, over several concentrations for each form of vitamin D, as measured by the methods disclosed herein. For comparison, Table 2 reports cross-reactivity results for various vitamin D assay methods, including the present methods (right-most column).

TABLE 1

Cross Reactivity

| Test Substance | [Test Substance] ng/mL | Signal, RLU Mean | CV % | Conc., ng/mL Mean | CV % | % Recovery |
|---|---|---|---|---|---|---|
| 25-Hydroxy | 150 | 2432 | 11.9 | 104.5 | 20.9 | 70 |
| vitamin D3 | 100 | 2941 | 2.7 | 76.5 | 3.4 | 77 |
| | 50 | 4044 | 5.2 | 55.5 | 4.4 | 111 |
| | 25 | 14076 | 9.4 | 20.8 | 13.0 | 83 |
| | 10 | 20071 | 5.1 | 11.0 | 11.4 | 110 |
| | 0 | 28281 | 2.8 | 4.2 | 9.3 | |
| 1α,25-Dihydroxy | 150 | 2352 | 4.2 | 107.1 | 7.4 | 71 |
| Vitamin D3 | 100 | 3642 | 3.0 | 60.6 | 2.8 | 61 |
| | 50 | 7804 | 18.0 | 36.5 | 11.6 | 73 |
| 24,25-Dihydroxy | 150 | 22992 | 6.2 | OORL | | |
| Vitamin D3 | 100 | 23735 | 2.3 | OORL | | |
| | 50 | 25059 | 3.2 | OORL | | |
| Cholecalciferol | 150 | 31607 | 9.8 | OORL | | |
| (Vitamin D3) | 100 | 30864 | 2.4 | OORL | | |
| | 50 | 31046 | 3.6 | OORL | | |
| Ergocalciferol | 150 | 30935 | 4.0 | OORL | | |
| (Vitamin D2) | 100 | 27040 | 1.0 | OORL | | |
| | 50 | 30040 | 3.9 | OORL | | |

("OORL" (out of range - low) indicates that the analyte concentration was below the detection limit)

TABLE 2

Reported Vitamin D Metabolite Cross Reactivity for Various Methods

| Vitamin D Metabolite | DiaSorin 25-Hydroxyvitamin D 125I RIA | DiaSorin Liaison ® 25 OH Vitamin D TOTAL | Roche Vitamin D3 (25-OH) | IDS ELISA kit | Present Methods |
|---|---|---|---|---|---|
| Vitamin D3 | 0.8% | <1% | <1% | <0.01% | <0.01% |
| Vitamin D2 | 0.8% | <1% | <1% | <0.3% | <0.01% |
| 25(OH) D3 | 100% | 100% | 100% | 100% | 100% |
| 25(OH) D2 | 100% | 104% | <10% | 75% | 110% |
| 1,25(OH)2 D3 | 11% | 17% | up to 100% | NR | 70% |
| 1,25(OH)2 D2 | 11% | 40% | NR | NR | NR |
| 24,25(OH)2 D3 | NR | NR | NR | >100% | NR |

As stated in the manufacturer's product insert.
NR = Not Reported.

Example 5: Reagent Stability

The stability of pepsin in frozen aliquots of aqueous pepsin solution and of dry, lyophilized pepsin (e.g., a lyophilized powder formed from an aqueous pepsin solution) was measured. Pepsin was lyophilized in containers suitable for use when reconstituted, e.g., in an automated assay device. The pepsin was provided in a solution at a concentration of 10 mg/mL and was lyophilized into the containers to obtain the final reconstituted amount and concentration equal to the concentration and amounts used in the assay methods disclosed herein. The containers of lyophilized reagent were placed into cartridges (arrays including several such containers) and the reagent was reconstituted with 100 mM citrate buffer (pH 2.6). Clinical samples were used for comparison, and the vitamin D results were calculated for both conditions based on the standard curve obtained for frozen pepsin/buffer aliquots. There were no significant differences between the results obtained using the lyophilized reagent and the results obtained using the (thawed) frozen aliquot of pepsin reagent.

Figure 8:
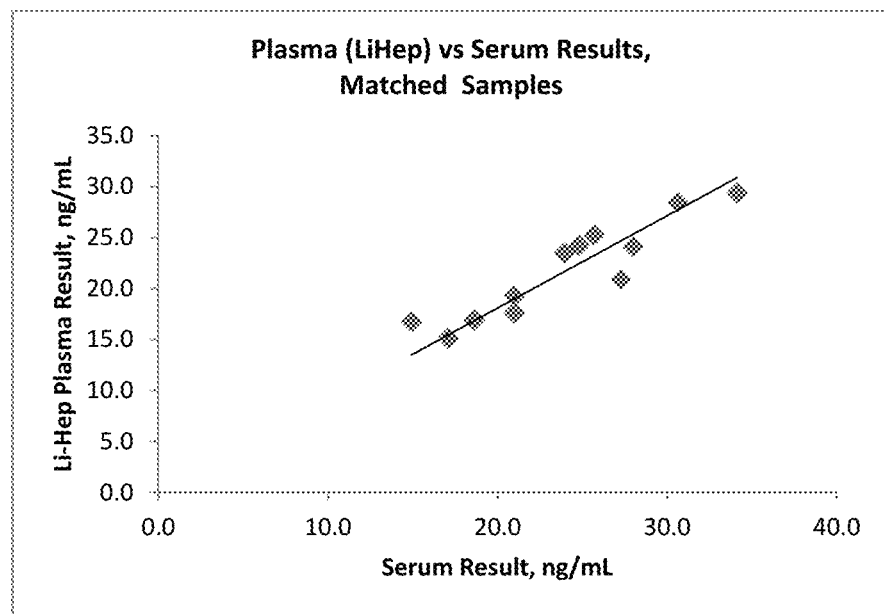
FIG. 8 shows comparisons between results using the present methods using pepsin treatment in matched samples (from the same donors) of plasma and of serum.

Example 6: Results Using Plasma, Whole Blood, Anticoagulants, and Sample Dilution Plasma:

Many blood tests must be performed using blood plasma, instead of serum, as results of some tests in serum may be inaccurate or irregular. In order to determine whether or not vitamin D assays using acidic pH and acid-active aspartyl peptidases may be performed using blood plasma as well as blood serum, assays using pepsin were performed in serum and in plasma. In these experiments, matched blood samples were collected from 12 donors in lithium heparin tubes (to prevent coagulation of plasma) and in serum tubes and centrifuged to obtain plasma and serum respectively. The matched samples were tested according to the methods disclosed herein and the results compared, based on the assay buffer calibration curve. There was no significant difference between serum and plasma results. Thus, the present vitamin D assays may be performed using either serum or plasma. These results are presented in FIG. 8.

Figure 9:
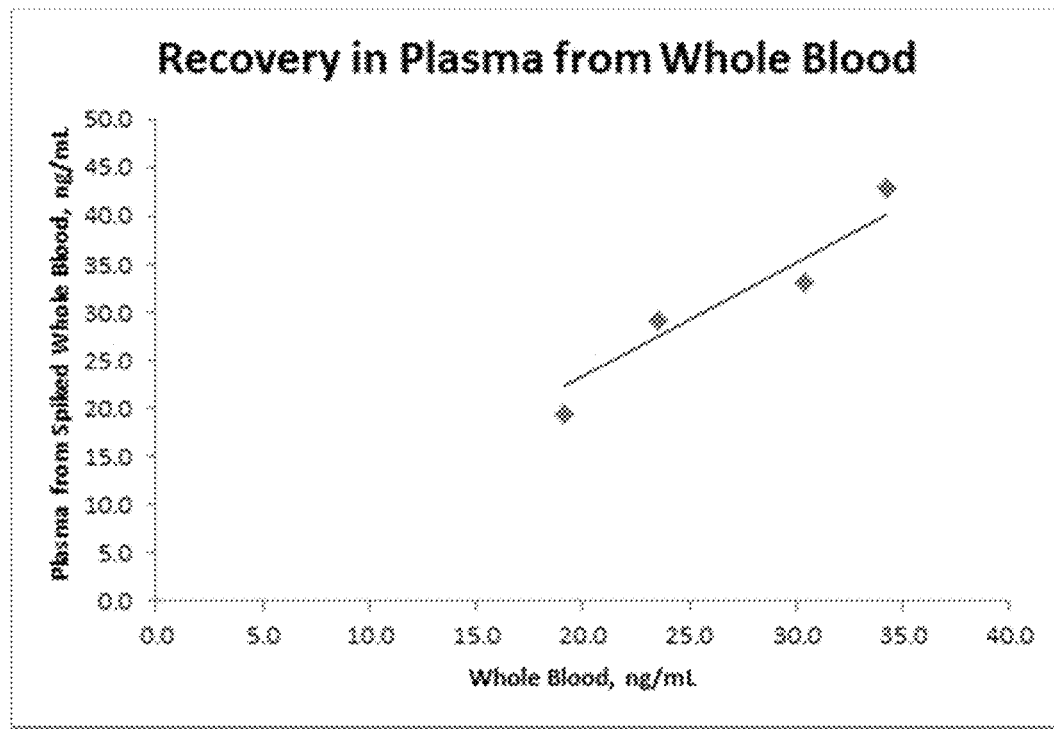
FIG. 9 shows comparisons between results obtained in whole blood (spiked with known amounts of vitamin D) and results obtained in plasma separated from whole blood using the present methods.

Whole Blood:

Whole blood must be treated to prepare plasma or serum from a blood sample as obtained from a subject. Tests on whole blood do not require such treatment, and thus may be simpler than tests performed on plasma or serum. In order to determine whether or not vitamin D assays using acidic pH and acid-active aspartyl peptidases may be performed using whole blood, in addition to using plasma or serum, vitamin D assays using pepsin were performed in whole blood and the results compared with matched results from plasma derived from the whole blood sample. In these experiments, blood samples were collected from donors, and matched whole blood and plasma samples were tested according to the methods disclosed herein. As shown in FIG. 9, there was no significant difference between whole blood and the plasma results. Thus, the present vitamin D assays may be performed using either whole blood or plasma. Together with the results shown in FIG. 8, the results presented herein demonstrate that vitamin D may be measured in whole blood, plasma, or serum according to the methods disclosed herein.

Effect of Anticoagulant:

Plasma prepared from blood is often treated with either EDTA or lithium heparin as an anticoagulant in the collection system. To test for any possible bias due to anticoagulant, matched samples were collected from 10 donors in EDTA and in lithium heparin tubes and centrifuged to prepare plasma prior to analysis for vitamin D. There was no significant difference between the lithium heparin and EDTA results.

Sample Dilution:

To test for dilution linearity across the range of vitamin D concentrations, a high concentration clinical sample was diluted to provide a total of six samples, the high concentration clinical sample and five dilutions of the high concentration sample, for a total of six samples with vitamin D concentrations of between about 14 ng/mL to about 108 ng/mL. The nominal concentration of vitamin D was calculated and the recovered concentration was compared to the calculated nominal concentration. The recovery was excellent and was linear across the range.

The assays disclosed herein performed well for whole blood, plasma and serum, and do not appear to be adversely affected by the presence of anticoagulants or of sample dilution. No other test method is believed to be able to make such vitamin D measurements using whole blood samples.

While the above is a description of embodiments as described herein, it is possible to use various alternatives, modifications and equivalents.

This document contains material subject to copyright protection. The copyright owner (Applicant herein) has no objection to the facsimile reproduction by anyone of the patent document or the patent disclosure, as they appear in the US Patent and Trademark Office patent file or records, but otherwise reserves all copyright rights whatsoever. The following notice shall apply: Copyright 2013-2015 Theranos, Inc.

The invention claimed is:

1. A method for determining the amount of vitamin D in a blood sample, wherein said blood sample comprises vitamin D and a vitamin D binding protein, the method comprising:
   contacting said blood sample with a low pH composition comprising an aspartyl peptidase active at low pH, whereby a low pH diluted blood sample composition is formed, effective to at least partially denature and at least partially digest said vitamin D binding protein;
   contacting said low pH diluted blood sample composition with a neutral pH composition comprising a neutral pH buffer, whereby a neutral pH diluted blood sample composition is formed, effective that said aspartyl peptidase is inactivated; and
   measuring the amount of said vitamin D in said neutral pH diluted blood sample, wherein said measuring comprises a competition assay measurement.

2. The method of claim 1, wherein said low pH composition comprising an aspartyl peptidase active at low pH comprises a buffer.

3. The method of claim 2, wherein said buffer comprises a buffer containing a citrate.

4. The method of claim 1, contacting said neutral pH diluted blood sample composition with a vitamin D binder, wherein said vitamin D binder binds specifically to vitamin D, wherein said vitamin D binder is selected from an antibody, an antibody fragment, and an aptamer.

5. The method of claim 1 further comprising:
   adding labeled vitamin D to said neutral pH diluted blood sample composition comprising said vitamin D binder wherein said labeled vitamin D comprises a label selected from a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher.

6. The method of claim 5, wherein said labeled vitamin D comprises an alkaline phosphatase label or a horseradish peroxidase label.

7. The method of claim 6 further comprising:
   contacting said neutral pH diluted blood sample composition comprising said vitamin D binder with a capture surface, wherein said capture surface comprises capture elements configured to bind to said vitamin D binder; and
   detecting said labeled vitamin D, wherein the amount of detected vitamin D provides a measure of the amount of vitamin D in the blood sample
   wherein detecting said labeled vitamin D comprises adding an alkaline phosphatase substrate or a peroxidase substrate.

8. The method of claim 7, wherein said capture elements configured to bind to said anti-vitamin D antibody are selected from a polynucleotide, a polypeptide, a peptide nucleic acid, a locked nucleic acid, an oligosaccharide, a polysaccharide, an antibody, an antibody fragment, an antibody mimic, an immunoadhesin, a receptor, a ligand, biotin, avidin, streptavidin, Extravidin, neutravidin, an avidin derivative, an avidin analog, a metal, and an epitope tag.

9. The method of claim 8, wherein said capture elements configured to bind to said anti-vitamin D antibody comprise avidin, streptavidin, biotin, an avidin derivative, or an analog thereof.

10. The method of claim 1, wherein said blood sample has a volume of less than about 25 µL.

11. The method of claim 1, wherein said blood sample has a volume of less than about 10 µL.

12. The method of claim 1, wherein said blood sample comprises a blood sample selected from a sample of whole blood, a sample of blood plasma, and a sample of blood serum.

13. The method of claim 1 wherein said aspartyl peptidase comprises porcine gastric pepsin.

14. The method of claim 2 wherein the buffer effective to provide a pH of between about pH 2.5 and about pH 4 after sample addition.

15. A method for determining the amount of vitamin D in a blood sample, wherein said blood sample comprises vitamin D and a vitamin D binding protein, the method comprising:
   contacting said blood sample with a low pH composition comprising an aspartyl peptidase active at low pH, whereby a low pH diluted blood sample composition is formed, effective to at least partially denature and at least partially digest said vitamin D binding protein;
   contacting said low pH diluted blood sample composition with a neutral pH composition comprising a neutral pH buffer, whereby a neutral pH diluted blood sample composition is formed, effective that said aspartyl peptidase is inactivated; and
   measuring the amount of said vitamin D in said neutral pH diluted blood sample, wherein said measuring comprises a competition assay measurement;

wherein said low pH comprises a pH of about pH 5 or less.

16. A method for determining the amount of vitamin D in a blood sample, wherein said blood sample comprises vitamin D and a vitamin D binding protein, the method comprising:
- contacting said blood sample with a low pH composition comprising an aspartyl peptidase active at low pH, whereby a low pH diluted blood sample composition is formed, effective to at least partially denature and at least partially digest said vitamin D binding protein;
- contacting said low pH diluted blood sample composition with a neutral pH composition comprising a neutral pH buffer, whereby a neutral pH diluted blood sample composition is formed, effective that said aspartyl peptidase is inactivated; and
- measuring the amount of said vitamin D in said neutral pH diluted blood sample, wherein said measuring comprises a competition assay measurement;
- performing another assay for the measurement of another analyte in the blood sample.

\* \* \* \* \*